United States Patent
Kapp et al.

(10) Patent No.: US 7,090,853 B2
(45) Date of Patent: Aug. 15, 2006

(54) NOSCAPINE DERIVATIVES AS ADJUVANT COMPOSITIONS AND METHODS OF USE THEREOF

(75) Inventors: Judith Kapp, Atlanta, GA (US); Yong Ke, Carmel, IN (US)

(73) Assignee: Emory University, GA (US)

( * ) Notice: Subject to any disclaimer, the term of this patent is extended or adjusted under 35 U.S.C. 154(b) by 169 days.

(21) Appl. No.: 10/288,442

(22) Filed: Nov. 6, 2002

(65) Prior Publication Data

US 2003/0130344 A1    Jul. 10, 2003

Related U.S. Application Data

(62) Division of application No. 09/558,042, filed on Apr. 26, 2000, now abandoned.

(60) Provisional application No. 60/130,980, filed on Apr. 26, 1999.

(51) Int. Cl.
*A61K 31/445* (2006.01)
*A61K 39/145* (2006.01)
*A61K 39/165* (2006.01)
*A61K 39/193* (2006.01)
*A61K 39/205* (2006.01)

(52) U.S. Cl. .................. 424/204.1; 424/206.1; 424/209.1; 424/212.1; 424/218.1; 424/224.1; 424/232.1; 424/234.1; 424/236.1; 424/240.1; 424/256.1; 424/259.1; 424/261.1; 424/278.1; 424/281.1; 424/282.1; 514/291; 514/310; 514/319; 514/320; 514/466; 514/465; 514/885

(58) Field of Classification Search ................ 514/310, 514/291, 466, 465, 282.1, 319, 320, 885; 424/204.1, 206.1, 209.1, 212.1, 218.1, 224.1, 424/232.1, 234.1, 236.1, 240.1, 256.1, 259.1, 424/261.1, 278.1, 281.1
See application file for complete search history.

(56) References Cited

U.S. PATENT DOCUMENTS

| | | | |
|---|---|---|---|
| 6,376,516 B1 * | 4/2002 | Joshi et al. | 514/320 |
| 6,548,066 B1 * | 4/2003 | Michaeli et al. | 424/185.1 |
| 6,673,814 B1 * | 1/2004 | Joshi et al. | 514/320 |
| 2002/0137762 A1 * | 9/2002 | Joshi et al. | 514/291 |

FOREIGN PATENT DOCUMENTS

| | | | |
|---|---|---|---|
| GB | 1148824 | * | 4/1969 |
| WO | WO 99/08528 | | 2/1999 |

OTHER PUBLICATIONS

Winter et al., Journal of Experimental Medicine (1955), 101, pp. 17-24.*
Van Essen et al., Dutch Standard in Influenza and Influence Vaccination, Huisarts en Wetenschap, (1993) 36/10 pp. 342-346.*
Porter et al "Mropological transformation of an established Syrian hamster dermal cell with the anti-tussive agent noscapine", abstract Mutagenesis, 1992, vol. 7(3), pp. 205-209, Database Caplus on STN, School Biol. Sci, Univ.,(Swansea UK), AN192:462728.
Ghosh et al "Noscapine a New Antitumor Agent in the Treatment of Ovarian Cancer" Proceedings Of the American Association For Cancel Research Annual Meeting, vol. 40, Mar. 1999 p. 206.

* cited by examiner

*Primary Examiner*—Frederick Krass
(74) *Attorney, Agent, or Firm*—Antonelli, Terry, Stout and Kraus, LLP.

(57) ABSTRACT

An adjuvant composition comprising noscapine and its derivatives, for use in the treatment of tumors, cancer, as an adjuvant for vaccines.

2 Claims, 5 Drawing Sheets

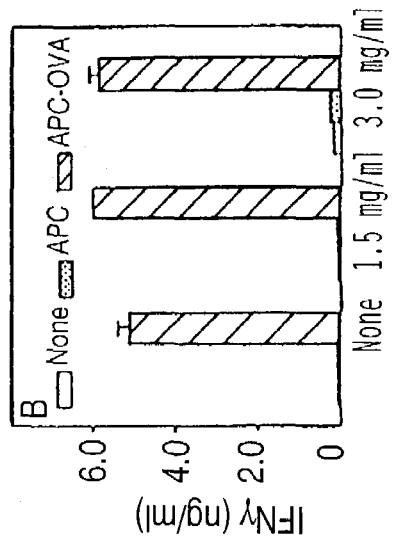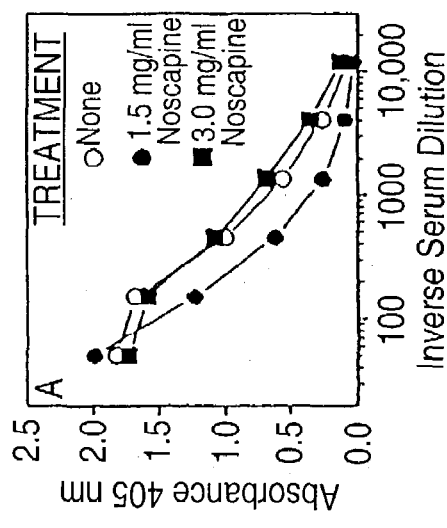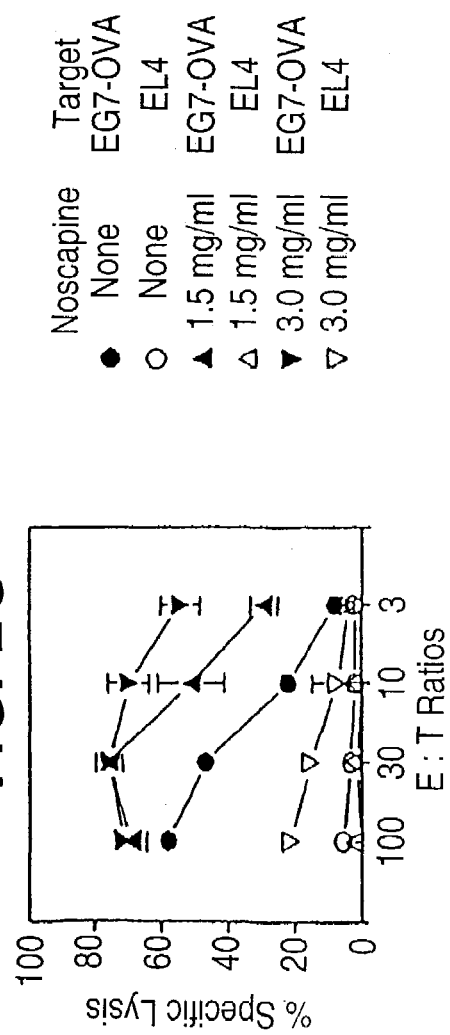

NOSCAPINE DERIVATIVES AS ADJUVANT COMPOSITIONS AND METHODS OF USE THEREOF

CROSS-REFERENCE TO RELATED APPLICATIONS

This application is a Divisional Application of application Ser. No. 09/558,042, filed Apr. 26, 2000, now abandoned, which application claimed the benefit of the filing date of provisional application Ser. No. 60/130,980, filed on Apr. 26, 1999 and included subject matter related to application Ser. No. 60/057,037. All of these applications are incorporated herein by reference.

The research conducted for the present invention was supported in part by a grant from National Institutes of Health.

FIELD OF THE INVENTION

The present invention relates to an adjuvant composition comprising noscapine and its derivatives, for use in the treatment of tumors, cancer, as an adjuvant for vaccines.

BACKGROUND

Some antigens are highly immunogenic and are capable alone of eliciting protective immune responses. Other antigens, however, fail to induce a protective immune response or induce only a weak immune response. A frequent difficulty with active immunization protocols is that the vaccine antigen does not possess sufficient immunogenicity to promote a strong immune response, and therefore a sufficient level of protection against subsequent challenge by the same antigen. In addition, certain antigens may elicit only weak cell-mediated or antibody response. For many antigens, both a strong humoral response and a strong cell-mediated response is desirable.

For decades, researchers have experimented with diverse compounds to increase the immunogenicity of vaccines, as well as other pharmaceutical compositions. Immunopotentiators, also known as adjuvants, of vaccines are compositions of matter that facilitate a strong immune response to a vaccine. In addition, the relatively weak immunogenicity of certain novel recombinant antigens has required adjuvants to be more potent. Vaccine adjuvants have different modes of action, affecting the immune response both quantitatively and qualitatively. Such modes of action can be by mobilizing T cells, acting as depots and altering lymphocyte circulation so that these cells remain localized in draining lymph nodes. They may also serve to focus antigen at the site of immunization, thereby allowing antigen specific T cells and B cells to interact more efficiently with antigen-presenting cells. Adjuvants may also stimulate proliferation and differentiation of T cells and have effects on B cells, such as enhancing the production of different Ig isotypes. Further, adjuvants may stimulate and affect the behavior of antigen-presenting cells, particularly macrophages, rendering them more effective for presenting antigen to T cells and B cells.

In the development of some vaccines and immunogenic compositions, there is a trend to use smaller and well defined immunogenic and protective materials. Recent advances in molecular genetics, protein biochemistry, peptide chemistry, and immunobiology have provided economical and efficient technologies to identify and produce large quantities of pure antigens from various pathogens. However, some such materials may not be sufficiently immunogenic, due to either their small size (especially synthetic peptides) or the lack of intrinsic immunostimulatory properties thereof.

Immunogenicity can be significantly improved if these antigens are co-administered with adjuvants. Adjuvants can also attract cells of the immune system to an antigen depot and stimulate such cells to elicit immune responses.

Immunostimulatory agents or adjuvants have been used for many years to improve the host immune responses to, for example, vaccines. Intrinsic adjuvants, such as lipopolysaccharides, normally are the components of the killed or attenuated bacteria used as vaccines. Extrinsic adjuvants are immunomodulators which are typically non-covalently linked to antigens and are formulated to enhance the host immune responses. Thus, adjuvants have been identified that enhance the immune response to antigens delivered parenterally. Some of these adjuvants are toxic, however, and can cause undesirable side-effects, making them unsuitable for use in humans and many animals. Indeed, only aluminum hydroxide and aluminum phosphate (collectively commonly referred to as alum) are routinely used as adjuvants in human and veterinary vaccines. The efficacy of alum in increasing antibody responses to diptheria and tetanus toxoids is well established and, more recently, a HBsAg vaccine has been adjuvanted with alum. While the usefulness of alum is well established for some applications, it has limitations. For example, alum is ineffective for influenza vaccination and inconsistently elicits a cell mediated immune response. The antibodies elicited by alum-adjuvanted antigens are mainly of the IgG1 isotype in the mouse, which may not be optimal for protection by some vaccinal agents.

A wide range of extrinsic adjuvants can provoke potent immune responses to antigens. These include saponins complexed to membrane protein antigens (immune stimulating complexes), pluronic polymers with mineral oil, killed mycobacteria in mineral oil, Freund's complete adjuvant, bacterial products, such as muramyl dipeptide (MDP) and lipopolysaccharide (LPS), as well as lipid A, and liposomes.

To efficiently induce humoral immune responses (HIR) and cell-mediated immunity (CMI), immunogens are emulsified in adjuvants. Many adjuvants are toxic, inducing granulomas, acute and chronic inflammations (Freund's complete adjuvant, FCA), cytolysis (saponins and Pluronic polymers) and pyrogenicity, arthritis and anterior uveitis (LPS and MDP). Although FCA is an excellent adjuvant and widely used in research, it is not licensed for use in human or veterinary vaccines because of its toxicity. Freund's Complete adjuvant (FCA) is an emulsion containing mineral oil and killed mycobacteria in saline. Freund's incomplete adjuvant (FIA) omits the mycobacteria. Both FIA and FCA induce good humoral (antibody) immunity, and FCA additionally induces high levels of cell-mediated immunity. However, neither FCA nor FIA are acceptable for clinical use due to the side effects. In particular, mineral oil is known to cause granulomas and abscesses, and *Mycobacterium tuberculosis* is the agent responsible for tuberculosis.

There have been many substances that have been tried to be used as adjuvants, such as the lipid-A portion of gram negative bacterial endotoxin, and trehalose dimycolate of mycobacteria. The phospholipid lysolecithin exhibited adjuvant activity (Arnold et al., Eur. J. Immunol. 9:363–366, 1979). Some synthetic surfactants exhibited adjuvant activity, including dimethyldioctadecyl ammonium bromide (DDA) and certain linear polyoxypropylenepolyoxyethylene (POP-POE) block polymers (Snippe et al., Int. Arch. Allergy Appl. Immunol. 65:390–398, 1981; and Hunter et al., J. Immunol. 127:1244–1250, 1981) While these natural or synthetic surfactants demonstrate some degree of adjuvant activity, they do not demonstrate the degree of immunopotentiation (i.e., adjuvant activity) as FCA or FIA.

Another approach has looked to break down the adjuvant effect from mycobacteria and determine adjuvant activity from a muramyl-peptide in the cell wall. The smallest fragment of this molecule that retains adjuvant activity is N-acetyl-muramyl-L-alanyl-D-isoglutamine, which is also called muramyl dipeptide (MDP) (Ellouz et al., Biochem. & Biophys. Res. Comm. 1317–1325, 1974). There have been many MDP derivatives prepared as vaccine adjuvants and described in U.S. Pat. Nos. 4,158,052; 4,323,559; 4,220,637; 4,323,560; 4,409,209; 4,423,038; 4,185,089; 4,406,889; 4,082,735; 4,082,736; 4,427,659; 4,461,761; 4,314,998; 4,101,536; and 4,369,178. Each of these disclosed MDP derivatives were weakly effective at stimulating the immune system when administered in aqueous solution, but the activity generally falls short of FCA or FIA.

Vaccine adjuvants are useful for improving an immune response obtained with any particular antigen in a vaccine composition. Adjuvants are used to increase the amount of antibody and effector T cells produced and to reduce the quantity of antigen and the frequency of injection. Although some antigens are administered in vaccines without an adjuvant, there are many antigens that lack sufficient immunogenicity to stimulate a useful immune response in the absence of an effective adjuvant. Adjuvants also improve the immune response from "self-sufficient" antigens, in that the immune response obtained may be increased or the amount of antigen administered may be reduced.

Many tumors express proteins that can serve as tumor-specific antigens. Such antigens can be processed via the MHC class I pathway and presented to CD8+ T cells as has been shown for the MAGE-1 gene expressed in melanoma (1), p53 in breast cancer (2), heat shock proteins (3,4), and glycosylation variants of proteins such as MUC-1 mucin (5).

However, tumors generally lack co-stimulatory molecules and hence cannot provide the requisite two signals to activate humor-specific CTL (6). Consequently, spontaneous tumors generally fail to stimulate immunity.

Tumors have been genetically engineered to express co-stimulators [reviewed in (7) {8276/id Viret & Lindemann 1997} (8)] and the modified cells can induce rejection if given before the tumor is transplanted in model systems (9). In a clinical setting, however, tumors presenting antigen in the absence of co-stimulators will likely induce tolerance of the relevant T cells before the tumor is detected (10). Such tumor-specific tolerance may prevent induction of immunity by genetically engineered, autologous tumor cells. Tolerance induction by tumors is not well characterized but recent reports (11,12) demonstrate that tumors induced tolerance in certain animal models.

The present inventors have recently found that the antitussive noscapine and its derivatives are useful in the treatment of neoplastic diseases. Noscapine is used as an antitussive drug and has low toxicity in humans. Noscapine arrests mammalian cells at mitosis, causes apoptosis in cycling cells, and has potent antitumor activity. Noscapine is an alkaloid from opium, and is readily available as a commercial byproduct in the commercial production of prescription opiates. It has been discovered that noscapine promotes assembly of tubulin subunits.

The present inventors have now discovered that noscapine and its derivatives are useful as adjuvant compositions to augment cell mediated immunity. In particular, noscapine and its derivatives can be used to enhance cytolytic responses to a tumor cell or as a vaccine adjuvant.

SUMMARY OF THE INVENTION

The present invention provides an adjuvant composition to augment cell mediated immunity comprising a noscapine compound of the formula 1:

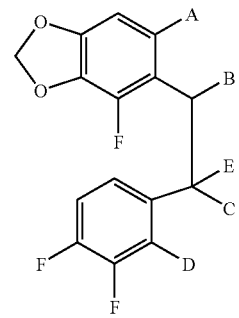

wherein: A is
(i)

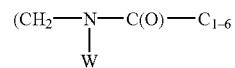

alkyl; and W is $C_{1-6}$ alkyl;
(ii)

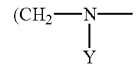

and forms a six membered ring with B, said ring containing one nitrogen;
Y is
(a) $C_{1-6}$ alkyl, or H;
(b) $C(O)$—$C_{1-6}$ alkyl;
(c)

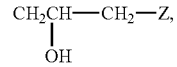

wherein Z is $C_{1-6}$ alkyl or O—$C_{1-6}$ alkyl;
(d) aryl; or
(e) heterocycle;
B is a single bond, OH or halo;
C is —OH, —$CH_2$— or forms a 5-membered lactone or lactam ring with D; and
D is:
  (i) —OH, —$CH_2$-halo, —CH(O)—, —COOH, —C(O)—O—$C_{1-6}$ alkyl, —$(CH_2)_n$—, —CHOH—, wherein n is an integer and is 1, 2, or 3; or
  (ii) forms a 5-membered lactone or lactam ring with D;
E is —H or —$CH_3$; and
F is —OH or —$OCH_3$, or pharmaceutically acceptable salts thereof.

In another embodiment the invention provides a method of augmenting cell mediated immunity to bacteria, or viruses that infect host cells which lack co-stimulatory molecules comprising administering an effective amount of the noscapine or derivatives thereof. In the method of the invention noscapine may be administered with an attenuated or live vaccine.

In another aspect, the invention provides a method of augmenting cell mediated immunity against tumor cells that lack co-stimulatory molecules comprising administering an effective amount of noscapine or derivatives thereof.

The invention provides for a method of preventing metastasis of a tumor comprising administering an effective amount of noscapine or derivatives thereof.

The present invention also provides a method of enhancing cytolytic responses to a tumor comprising administering an effective amount of noscapine or derivatives thereof.

Advantageously, the invention provides a method of immunization with proteins or polysaccharides, comprising administering said protein or polysaccharide vaccine with an effective amount of noscapine or derivatives thereof.

The above and other objects of the invention will become readily apparent to those of skill in the relevant art from the following detailed description and figures, wherein only the preferred embodiments of the invention are shown and described, simply by way of illustration of the best mode of carrying out the invention. As is readily recognized the invention is capable of modifications within the skill of the relevant art without departing from the spirit and scope of the invention.

BRIEF DESCRIPTION OF THE FIGURES

FIG. 2 shows control B6 mice and tumor survivors treated for four months with noscapine were injected with OVA in CFA. Two weeks later, (FIG. 2A) antibody responses were measured by ELISA with OVA coated microtiter plates, (FIG. 2B) IFNγ production by lymphnode cells was measured by ELISA by comparison with recombinant IFNγ and (FIG. 2C) CTL responses were measured using $^{51}$Cr labeled target cells. Mice injected with tumors and treated with Noscapine produced enhanced CTL responses after immunization with OVA in CFA but levels of antibody and IFNγ that were indistinguishable from control mice.

DESCRIPTION OF THE INVENTION

Figure 1:
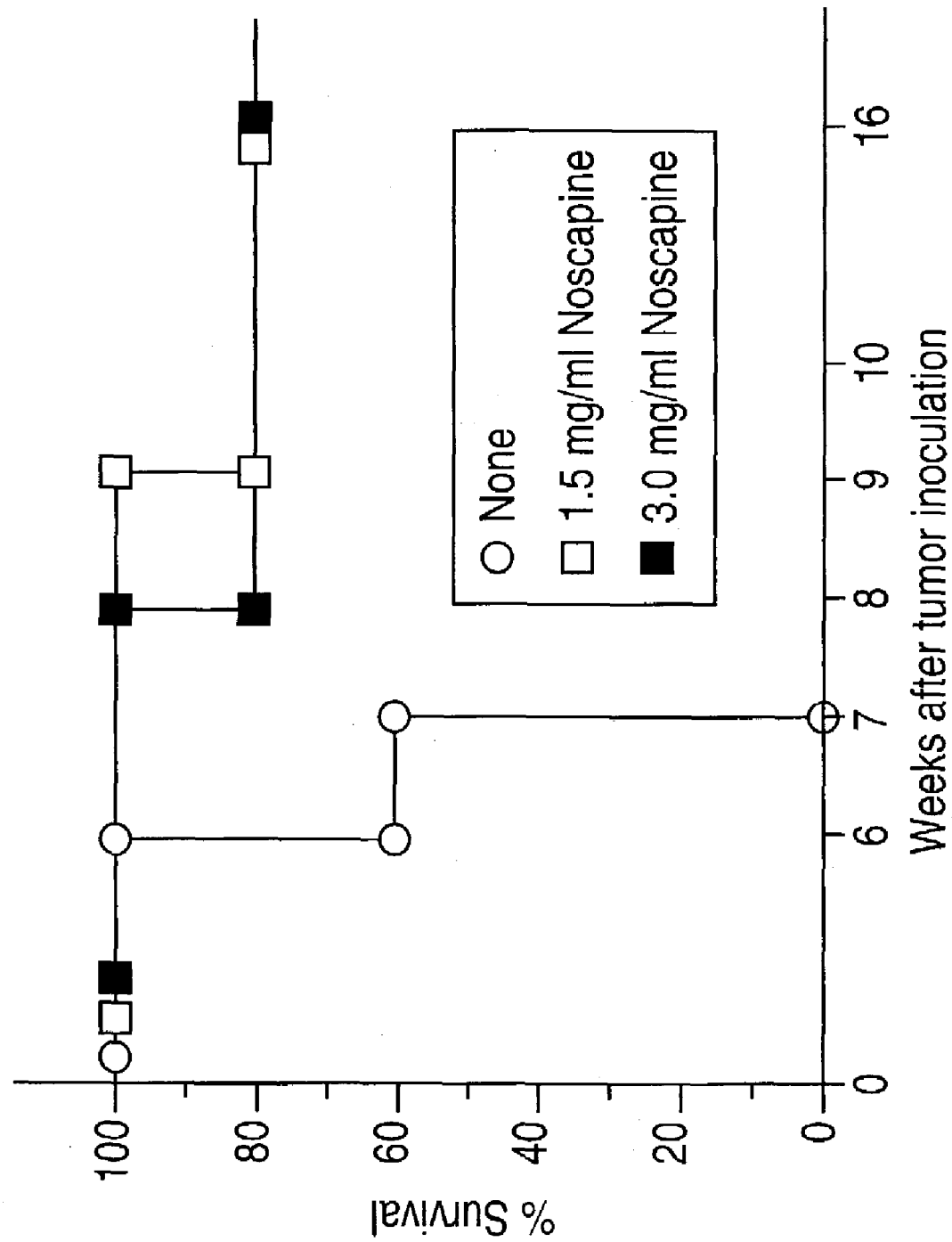
FIG. 1 shows that noscapine prolongs survival of tumor-bearing mice. C57BL/6 mice were injected s.c. with $2 \times 10^6$ E.G7-OVA tumor cells. Three days later, two groups received the indicated dose of noscapine in their drinking water. There were 5 mice/group. Untreated mice survived from 6 to 7 weeks after tumor inoculation. In marked contrast, the majority of the mice treated with 1.5 or 3.0 mg/ml Noscapine survived for greater than 16 weeks when the experiment was terminated.
Figure 3A:
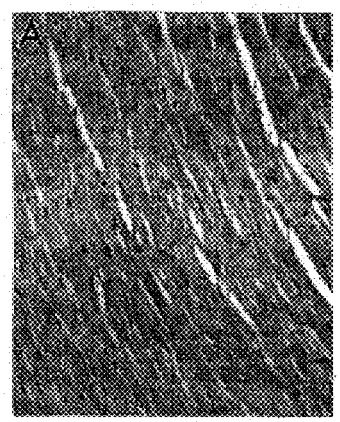
FIGS. 3A–3I show B6 mice were injected subcutaneously with $2 \times 10^6$ E.G7-OVA tumor cells and after three days half of the mice were treated continuously with 1.5 or 3.0 mg noscapine/ml of drinking water. All of the untreated mice developed tumors and were euthanized after three weeks. The majority of tumors in mice treated with noscapine regress. Normal B6 mice (A–C) and mice treated for 3 months with noscapine (D–F) were euthanized. Heart (A, D), kidney (B, E), and liver (C–F) were embedded in paraffin and stained with H & E. Photographs were taken at (60×) and show no significant differences between normal and noscapine treated mice.
Figure 3B:
Figure 3C:
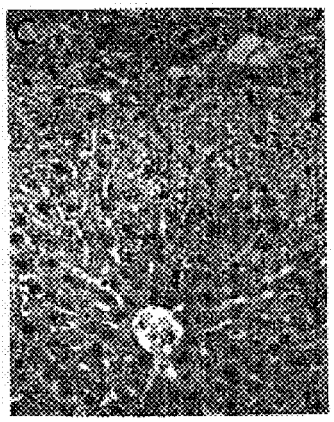
Figure 3D:
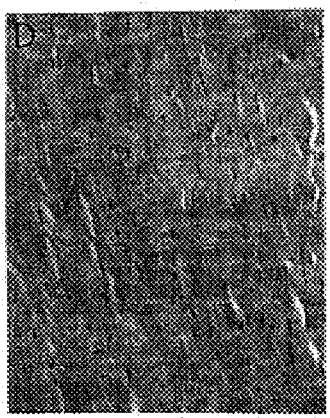
Figure 3E:
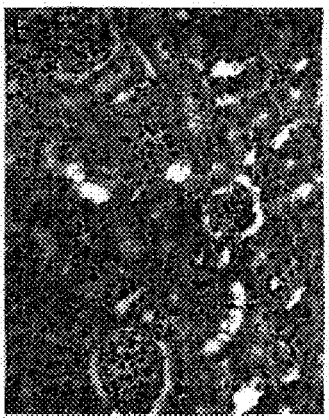
Figure 3F:
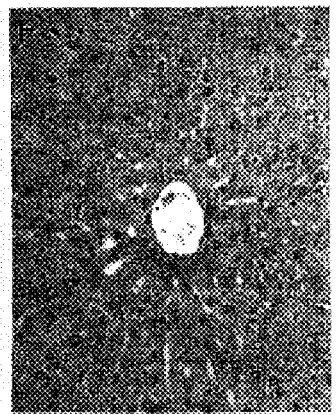
Figure 3G:
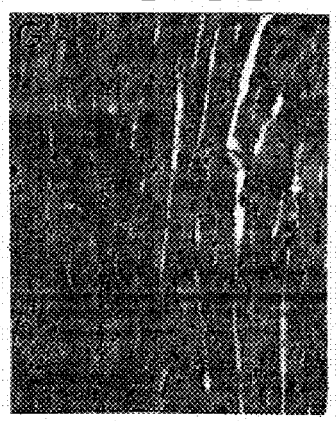
Figure 3H:
Figure 3I:
Figure 4A:
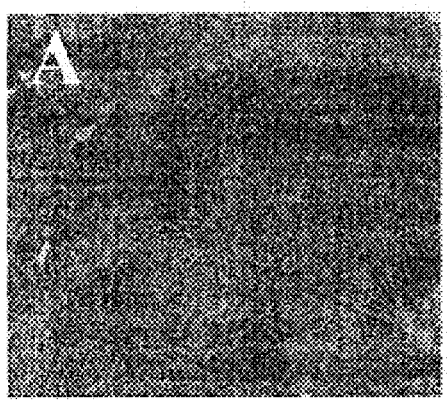
FIGS. 4A–4D show B6 mice were treated with 1.5 mg noscapine/ml in their drinking water or acidified water, as a negative control. One week later mice were injected with OVA in CFA. Mice were sacrificed two weeks later. Spleen (upper panels) and small intestine (lower panels) were embedded in paraffin and stained with H & E. Photographs were taken at (25×) and show no significant differences between control (upper left) and noscapine (upper right) treated spleens. Thus, Noscapine had no detectable toxic effect on lymphoid cells that are proliferating in response to immunization. The small intestines of the noscapine treated mice developed edema, increased frequency of goblet cells, and prominent crypt cells (lower right) compared to the control (lower left). The response of the gut to Noscapine is one of mild irritation.
Figure 4B:
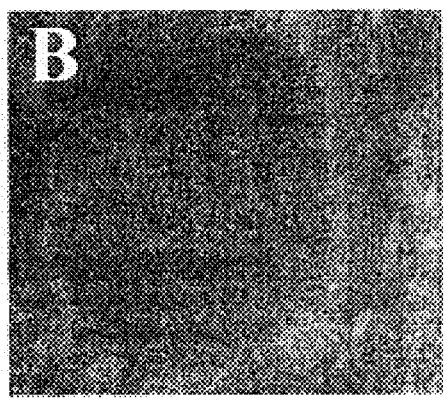
Figure 4C:
Figure 4D:

The present invention relates to an adjuvant or pharmaceutical composition comprising a compound of the formula

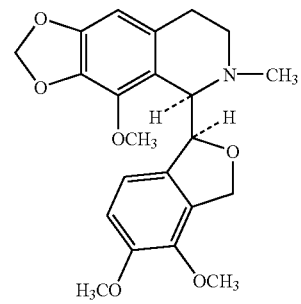

wherein: A is (I)

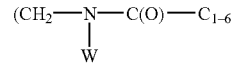

alkyl; and W is $C_{1-6}$ alkyl;

(ii)

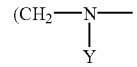

and forms a six membered ring with B, said ring containing one nitrogen;

Y is (a) $C_{1-6}$ alkyl, or H;

(b) $C(O)-C_{1-6}$ alkyl;

(c)

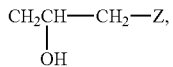

wherein Z is $C_{1-6}$ alkyl or O—$C_{1-6}$ alkyl;
(d) aryl; or
(e) heterocycle;

B is a single bond, OH or halo;
C is —OH, —CH$_2$— or forms a 5-membered lactone or lactam ring with D; and
D is:
  (I) —OH, —CH$_2$-halo, —CH(O)—, —COOH, —C(O)—O—C$_{1-6}$ alkyl, —(CH$_2$)$_n$—, —CHOH—, wherein n is an integer and is 1, 2, or 3; or
  (ii) forms a 5-membered lactone or lactam ring with D;
E is —H or —CH$_3$; and
F is —OH or —OCH$_3$, or pharmaceutically acceptable salts thereof, and a pharmaceutically acceptable carrier, said composition useful as an adjuvant composition. In a preferred embodiment the adjuvant of the invention excludes noscapine of the structure:

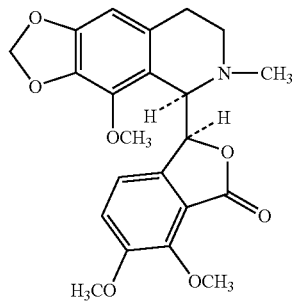

In the present invention, one preferred compound is:

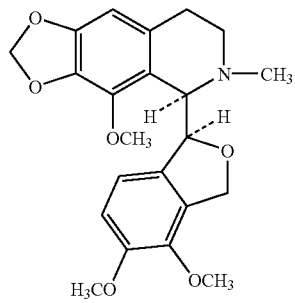

or pharmaceutically acceptable salt thereof.

The present invention also relates to a method for augmenting cell mediated immunity against tumor cells, comprising administering to a mammal in need of such treatment an effective amount of a composition comprising a compound of the formula:

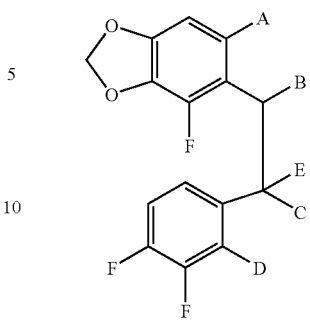

wherein: A is
(I)

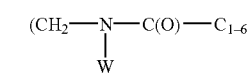

alkyl; and W is $C_{1-6}$ alkyl;
(ii)

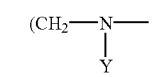

and forms a six membered ring with B, said ring containing one nitrogen;
Y is
(a) $C_{1-6}$ alkyl, or H;
(b) C(O)—$C_{1-6}$ alkyl;
(c)

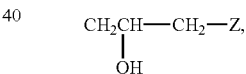

wherein Z is $C_{1-6}$ alkyl or O—$C_{1-6}$ alkyl;
(d) aryl; or
(e) heterocycle;

B is a single bond, OH or halo;
C is —OH, —CH$_2$— or forms a 5-membered lactone or lactam ring with D; and
D is:
  (I) —OH, —CH$_2$-halo, —CH(O)—, —COOH, —C(O)—O—C$_{1-6}$ alkyl, —(CH$_2$)$_n$—, —CHOH—, wherein n is an integer and is 1, 2, or 3; or
  (ii) forms a 5-membered lactone or lactam ring with D;
E is —H or —CH$_3$; and
F is —OH or —OCH$_3$, or pharmaceutically acceptable salts thereof, and a pharmaceutically acceptable carrier, said composition useful as an adjuvant composition and in a method of immunization.

The invention provides a method of enhancing a mammal's immune response to a vaccine antigen, comprising the steps of administering to such mammal an immunogenic amount of the vaccine antigen and an immunogenicity-augmenting amount of noscapine in concurrent or sequential combination with such vaccine antigen.

The antigen or drug suitable for use in the method of enhancing a mammal's response to a vaccine antigen, augmenting cell mediate immunity and method of immunization, are biologically active substances. These substances include biologically active polypeptide, antigens and vaccines. Any of the drugs used to treat the body can be incorporated in the present composition. The term "drug" is used herein in its broadest sense, as including any composition or substance that will produce a pharmacologic response. Suitable drugs for use with the composition of the invention include without limitation: protein drugs such as insulin; desensitizing agents such as antigens; vaccines such as smallpox, yellow fever, distemper, cholera, fowl pox, antivenom, scarlet fever, diphtheria toxoid, tetanus toxoid, whooping cough, influenza, rabies, mumps, measles and poliomyelitis; antibiotics, such as penicillin, tetracycline, neomycin and erythromycin; antiallergenics, steroids; decongestants; anti-cholinesterases; sedatives; tranquilizers; estrogens; humoral agents; antipsychotics; antispasmodics; antimalarials; antihistamines; cardioactive agents; nutritional agents such as vitamins, amino acids and fats. Other drugs having the same or different physiological activity as those recited above can be employed in drug delivery systems within he scope of the present invention. Suitable mixtures of drugs can also be incorporated into the composition in lieu of a single drug.

Preferably, the antigen is selected from the group consisting of a vaccine, bacteria, virus, rickettsia, pollen, dust, danders, a poison, and venom derived from an insect or snake. In a preferred embodiment the antigens which may be included as immunogenic compositions and in respect of which an immune response is modulated, also include microbial pathogens, proteins, glycoproteins lipoproteins, peptides, glycopeptides, lipopeptides, toxoids, carbohydrates, and tumor-specific antigens. Mixtures of two or more antigens may be employed. Peptides, glycopeptides or lipopeptides preferably include an amino acid sequence corresponding to an antigenic determinant of HIV, Rubella virus, Respiratory Syncytial Virus, *Bordetella pertussis, Haemophilus influenzae* or *Streptococcus pneumoniae*. In a preferred embodiment the antigen is a toxoid such as a pertussis toxoid, or a protein which is influenza hemagglutinin or a parainfluenza virus subunit, such as the HN or F proteins of PIV-3.

In the method of the present invention, one preferred compound is

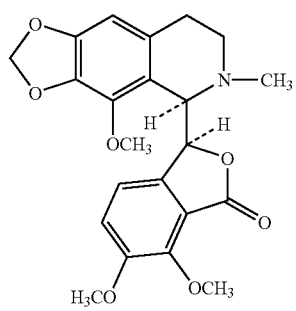

or pharmaceutically acceptable salts thereof.

The compounds of the present invention, may have asymmetric centers and occur as racemates, racemic mixtures and as individual diastereomers or enantiomers, with all isomeric forms being included in the present invention.

When any variable (e.g., W, Y, A, B, C, etc.) occurs more than one time in any constituent or in formula I, its definition on each occurrence is independent of its definition at every other occurrence. Also, combinations of substituents and/or variables are permissible only if such combinations result in stable compounds.

As used herein except where noted, "alkyl" is intended to include both branched and straight-chain saturated aliphatic hydrocarbon groups having the specified number of carbon atoms (Me is methyl, Et is ethyl, Pr is propyl, Bu is butyl); "Halo" as used herein means fluoro, chloro, bromo and iodo. As used herein, with exceptions as noted, "aryl" is intended to mean phenyl (Ph) or naphthyl.

The term heterocycle or heterocyclic, as used herein except where noted, represents a stable 5- to 7-membered mono- or bicyclic or stable 7- to 10-membered bicyclic heterocyclic ring system any ring which may be saturated or unsaturated, and which consists of carbon atoms and from one to three heteroatoms selected from the group consisting of N, O and S, and wherein the nitrogen and sulfur heteroatoms may optionally be oxidized, and the nitrogen heteroatom may optionally be quarternized, and including any bicyclic group in which any of the above-defined heterocyclic rings is used to a benzene ring. The heterocyclic ring may be attached at any heteroatom or carbon atom which results in the creation of a stable structure. Examples of such heterocyclic elements include but are not limited to piperidinyl, piperazinyl, 2-oxopiperazinyl, 2-oxopiperidinyl, 2-oxopyrrolodinyl, 2-oxoazepinyl, azepinyl, pyrrolyl, 4-piperidonyl, pyrrolidinyl, pyrazolyl, pyrazolidinyl, imidazolyl, imidazolinyl, imidazolidinyl, pyridyl, pyrazinyl, pyrimidinyl, pyridazinyl, oxazolyl, oxazolidinyl, isoxazolyl, isoxazolidinyl, morpholinyl, thiazolyl, thiazolidinyl, isothiazolyl, quinuclidinyl, isothiazolidinyl, indolyl, quinolinyl, isoquinolinyl, benziniidazolyl, thiadiazoyl, benzopyranyl, benzothiazolyl, benzoxazolyl, furyl, tetrahydrofuryl, tetrahydropyranyl, thienyl, benzothienyl, thiamorpholinyl, thiamorpholinyl sulfoxide, thiamorpholinyl sulfone, and oxadiazolyl.

The pharmaceutically-acceptable salts of the compounds of the present invention (in the form of water- or oil-soluble or dispersible products) include the conventional non-toxic salts or the quaternary ammonium salts which are formed, e.g., from inorganic or organic acids or bases. Examples of such acid addition salts include acetate, adipate, alignate, aspartate, benzenesulfonate, bisulfate, butyrate, citrate, camphorate, camphorsulfonate, cyclopentanepropionate, digluconate, dodecylsulfate, ethanesulfonate, fumarate, glucoheptanoate, glycerophosphate, hemisulfate, heptancate, hexanoate, hydrochloride, hydrobromide, hydroiodide, 2-hydroxyethane-sulfonate, lactate, maleate, methansolfonate, 2-naphthalenesulfonate, nucotinate, oxalate, pamoate, pectmate, persulfate, 3-phenylpropionate, picrate, pivalate, propionate, succinate, tartrate, thiocyanate, tosylate, and undecanoate. Base salts include ammonium salts, alkali metal salts such as sodium and potassium salts, alkaline earth metal salts such as calcium and magnesium salts, salts with organic bases such as dicyclohexylamine salts, N-methyl-D-glucamine, and salts with amino acids such as arginine, lysine, and so forth. Also, the basic nitrogen-containing groups may be quarternized with such agents as lower alkyl halides, such as methyl, ethyl, propyl, and butyl chloride, bromides and iodides; dialkyl sulfates like dimethyl, diethyl, dibutyl; and dizanyl sulfates, long chain halides such as decyl, lauryl, myristyl and stearyl chlorides, bromides and iodides, aralkyl ahlides like benzyl and phenethyl bromides and others.

Synthesis of Noscapine

Noscapine is an alkaloid occurring in abundance in the opium plant, *Papaver somniferum L. papaveraceae*. It can be extracted from the water-soluble residue remaining from the processing of opium in the commercial synthesis of morphine. It is readily available commercially in large quantities at low cost, from e.g., Aldrich Chemical Co., or Sigma Chemical Co. Noscapine can be separated from other opium alkaloids by the procedure according to Al-Yuhya, M. A., et al., in K. Florey (Ed.) Analytical Profiles of Drug Substances, Vol. 11 Academic Press 1982, pp. 407–461, or Sim, S. K. "Medicinal Plant Alkaloids," 2$^{nd}$ Ed. Un. Toronto Press 1970, p. 70.

Chemical synthesis of noscapinel is less desirable, although feasible. See, for example, Fleischhacker, W. et al., Chem. Monthly 120, 765 (19890); Shono, T. et al. Tetrahedron Lett. 21, 1351 (1980).

There are a variety of methods to synthesize noscapine. A one step synthetic reaction was published by W. H. Perkin and R. Robinson, *J. Chem. Soc.* (London), 99, 775 (1911). However, this method gave low yield and racemic mixtures. The reaction is shown as follows:

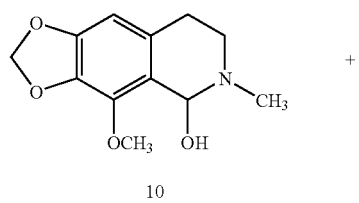

10

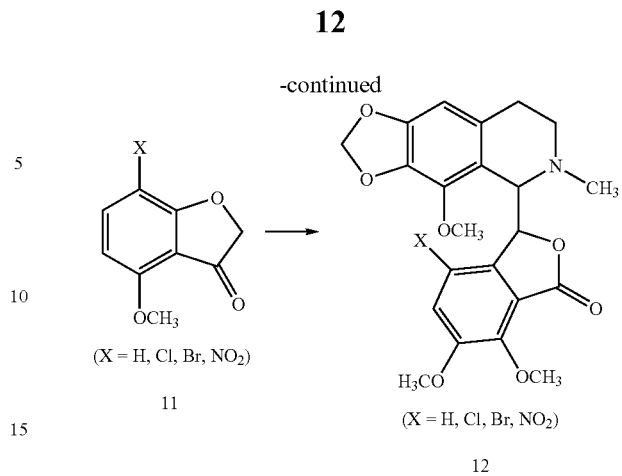

A second method was published by Von P. Kereks and R. Bognar. *J. Prakt. Chem.* 313, 923–928 (1971). In this method, 2-(3'-methoxy-4',5'-methylenedioxy-phenyl) ethylamine 13 reacts with meconine-3-carbonyl chloride 14 in benzene to gove N-(β-3-methoxy-4,5-methylenedioxyphenylethyl)-melconine-3-carbonylamide 15 with a yield of 86.6%. Compound 15 was cyclized by boiling with POCl$_3$ for 5 hr to produce compounds 16 and 17 with a yield of 46.7%. Compounds 16 and 17 are two isomers from cyclization of compound 15. These two isomers are reduced by either H$_2$/PtO$_2$ in acetic acid, or NaBH$_4$ in methanol. The reduced compound 18 was methylated by boiling with the mixture of HCHO and HCOOH, to produce noscapine 1 with a yield of 20.3%.

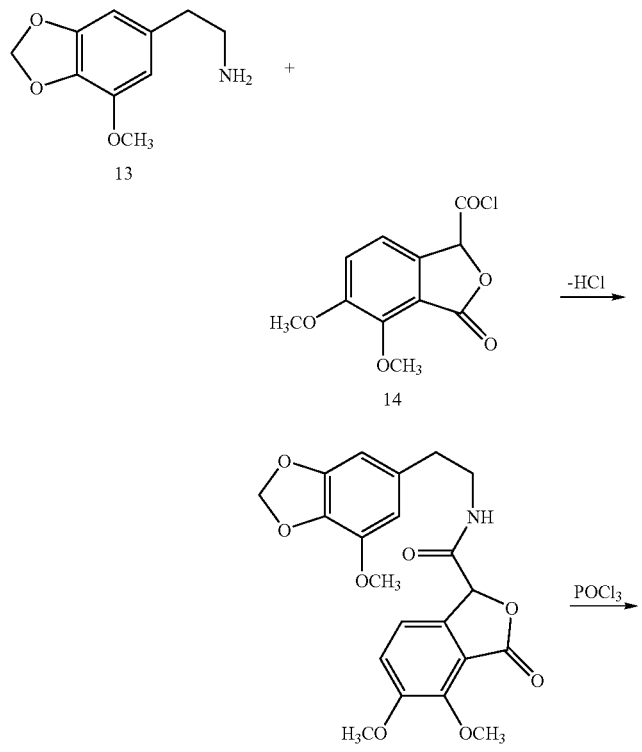

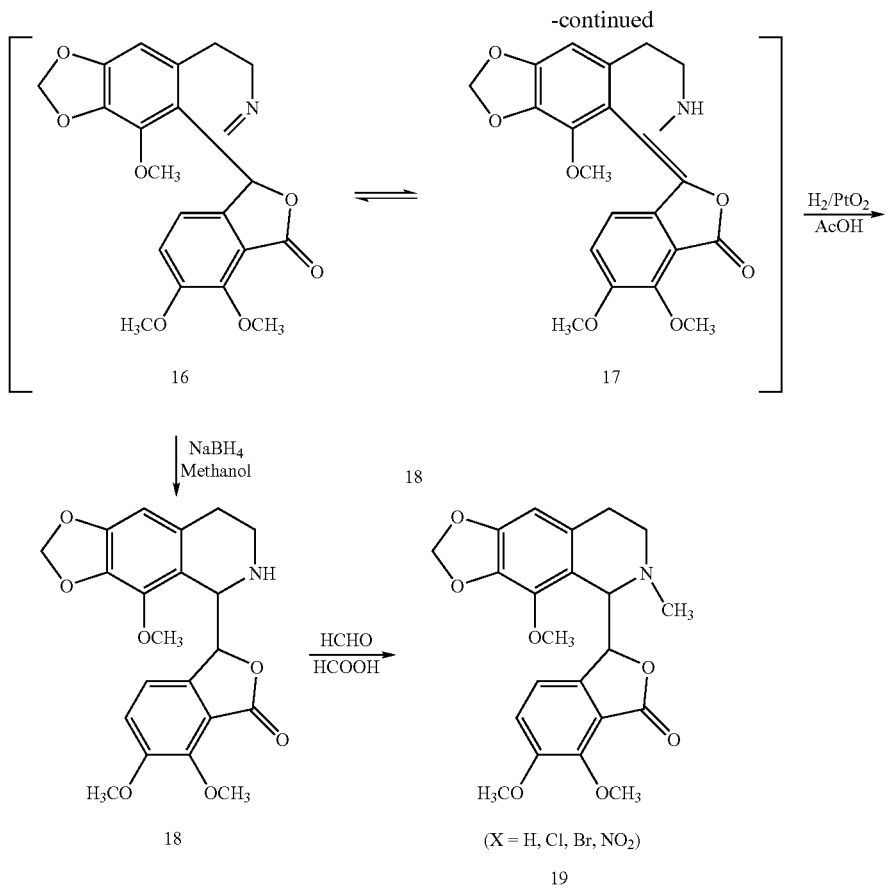

The compounds of the present invention are useful in the treatment of tumor cells and a variety of cancers, including but not limited to cancer of the colon, non-small cell lung cancer, cancer of the brain, ovarian cancer, cancer of the kidney, cancer of the prostate, leukemia, breast cancer, cancer of the bladder. For most of these kinds of neoplastic diseases' applicants have tested a variety of cell lines with noscapine, or derivatives thereof.

For these purposes, the compounds of the present invention may be administered orally, parenterally (including subcutaneous injections, intravenous, intramuscular, intrasternal injection or infusion techniques), by inhalation spray, or rectally, in dosage unit formulations containing conventional non-toxic pharmaceutically-acceptable carriers, adjuvants and vehicles.

Thus, in accordance with the present invention there is further provided a method of augmenting cell mediated immunity and a pharmaceutical composition including an adjuvant composition. There is also disclosed a method for treating tumor cells and preventing metastasis of related cancers. The treatment involves administering to a patient in need of such treatment a pharmaceutical composition comprising a pharmaceutical carrier and a therapeutically effective amount of a compound of the present invention, or a pharmaceutically acceptable salt thereof.

These pharmaceutical compositions may be in the form of orally-administrable suspensions or tablets; nasal sprays, sterile injectable preparations, for example, as sterile injectable aqueous or oleaginous suspensions or suppositories.

When administered orally as a suspension, these compositions are prepared according to techniques well-known in the art of pharmaceutical formulation and may contain microcrystalline cellulose for imparting bulk, alginic acid or sodium alginate as a suspending agent, methylcellulose as a viscosity enhancer, and sweeteners/flavoring agents known in the art. As immediate release tablets, these compositions may contain microcrystalline cellulose, dicalcium phosphate, starch, magnesium stearate and lactose and/or other excipients, binders, extenders, disintegrants, diluents and lubricants known in the art.

When administered by nasal aerosol or inhalation, these compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art.

The injectable solutions or suspensions may be formulated according to known art, using suitable non-toxic, parenterally-acceptable diluents or solvents, such as mannitol, 1,3-butanediol, water, Ringer's solution or isotonic sodium chloride solution, or suitable dispersing or wetting and suspending agents, such as sterile, bland, fixed oils, including synthetic mono- or diglycerides, and fatty acids, including oleic acid.

When rectally administered in the form of suppositories, these compositions may be prepared by mixing the drug with a suitable non-irritating excipient, such as cocoa butter, synthetic glyceride esters or polyethylene glycols, which are solid at ordinary temperatures, but liquify and/or dissolve in the rectal cavity to release the drug.

Dosage levels of the order of 0.02 to 5.0 or 10.0 grams-per-day are useful in the treatment or prevention of the above-indicated conditions, with oral doses two-to-five times higher. For example, compound 4 is effectively treated by the administration of from 10 to 50 milligrams of the compound per kilogram of body weight from one to three times per day. It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

EXAMPLE 1

Synthesis of Noscapine

Noscapine 1 was synthesized by the methods of Shono, T. et al, Tetrahedron Lett. 21, 1351 (1980); Fleishchacker, W. et al., Monatshefte fur Chemie 120, 765 (1989); Sam, J. et al, J. Pharm. Sci. 57: 1755 (1968); Al-Yuhya, M. A. et al., in K. Florey (Ed.) Analytical Profiles of Drug Substances, Vol. 11 Academic Press 1982, pp. 407–461; Battersby, A. R. et al., Tetrahedron Lett. 11, 669 (1965). It is readily available in large quantities from a variety of commercial sources, e.g. Aldrich Chemical Co. or Sigma Chemical Co. NCR data for (SAR)-Noscapine:

$^1$HNMR (CDCl$_3$, 300 MHz): δ 6.95 (d,J=8.1 Hz, 1 H), 6.27 (s, 1 H), 6.07 (d,J=8.4 Hz, 1 H), 5.90 (s, 2 H), 5.55 (d,J=3.9 Hz, 1 H) 4.37 (d,J=4.2 Hz, 1 H), 4.06 (s, 3 H), 4.00 (s, 3 H), 3.83 (s, 3 H), 2.60 (m, 1 H), 2.52 (s, 3 H), 2.38–2.27 (m, 2 H), 1.94–1.87 (m, 1 H).

$^{13}$C NCR (CDCl$_3$, 75.5 MHz): δ 168.0, 152.1, 148.3, 147.5, 140.9, 140.3, 133.9, 131.9, 120, 118.0, 117.6, 116.9, 102.2, 100.7, 81.7, 62.1, 60.7, 59.3, 56.7, 49.9, 46.2, 27.9.

EXAMPLE 2

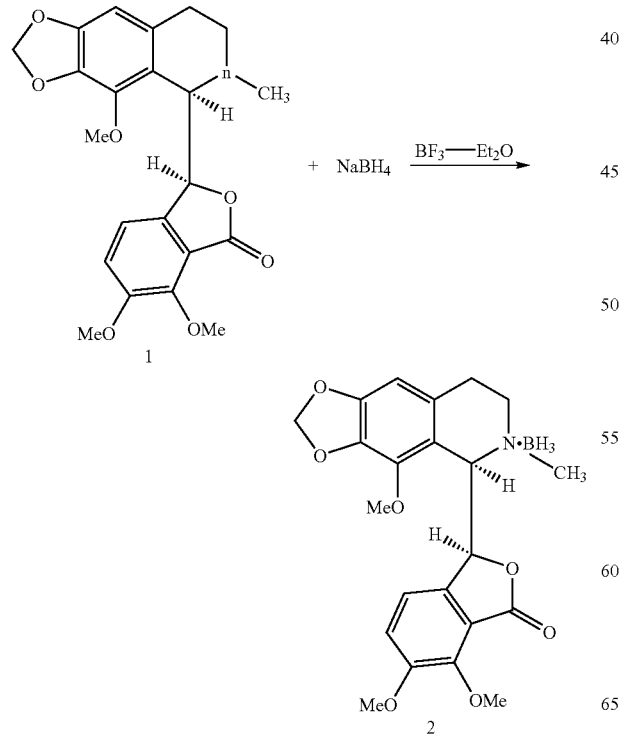

The synthesis of borane-(SAR)-noscapine complex (2):

(SAR)-Noscapine 1 (830 mg, 2.0 mmol, 1.0 equiv.) was dissolved in 10 mL of BF$_3$-Et$_2$O. This solution was dropped slowly at 0° to a solution of NaBH$_4$ (150 mg, 4.0 mmol, 2.0 equiv.) in 14 mL dry THF and stirred at 0° for 1 h under N$_2$. Then it was refluxed for 2 h. After cooling to room temperature, the solution was poured into ice water and extracted with CHCl$_3$ (70 mL×2). The organic phase was washed with brine, dried with MgSO$_4$ and concentrated. The resulting oil was purified by flash chromatography (SiO$_2$, 3×15 cm, 50% EtOAc in hexane) to give 2 as a white solid (444 mg, 52%). TLC (silica gel, 65% EtOAc in hexane, Rf=0.75); $^1$H NCR (CDCl$_3$, 300 MHz): δ 7.41 (d,J=8.1 Hz, 1 H), 7.31 ((d,J=8.1 Hz, 1 H), 6.83 (s, 1 H), 6.33 (s, 1 H), 5.81 (dd,J=12.9 Hz, 0.9 Hz, 2 H), 4.54 (s, 1 H), 3.99 (s, 3 H), 3.92 (s, 3 H), 3.73 (m, 1 H), 3.20 (s, 3 H), 3.15 (m, 2 H), 2.93 (m, 1 H), 2.61 (s, 3 H).

EXAMPLE 3

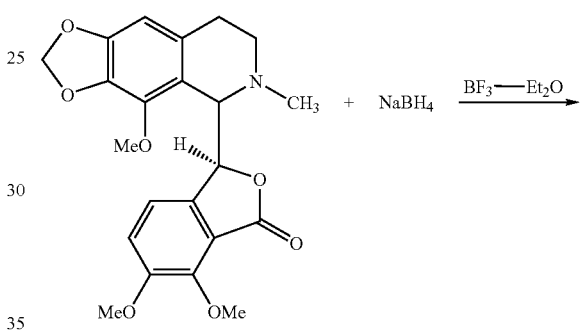

1

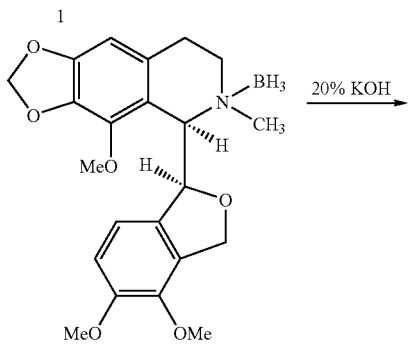

2

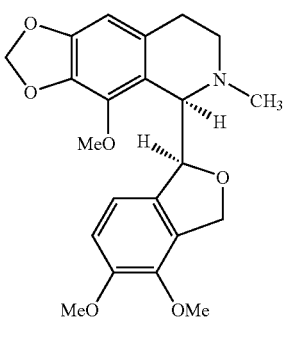

3

Compound 3 and 4 were prepared by literature method Prior, S.: Wiegrebe, W. *Arch. Pharm.* 1983, 316 737.:

The synthesis of 1,3-dihydro-4,5-dimethoxy-1-[1-(8-methoxy-2-methyl-6,7-methylenedioxy-1,2,3,4-tetrahydroisoquinoliyl)]isobenzofuran-BH$_3$ (3):

(SAR)-Noscapine (830 mg, 2.0 mmol, 1.0 equiv.) was dissolved in 10 mL of BF$_3$-Et$_2$O. This solution was dropped slowly at 0° C. for 1 h under N$_2$. Then it was refluxed for 4 h. After cooling to room temperature, the solution was poured into ice water and extracted with CHCl$_3$ (70 mL×2). The organic phase was washed with brine, dried with MgSO$_4$ and concentrated. The resulting oil was purified by flash chromatography (SiO$_2$, 3×15 cm, 50% EtOAc in hexane) to give 3 as a white solid (686 mg, 83%). TLC (silica gel, 50% EtOAc in hexane, Rf=0.80); IR (CH$_2$CL$_2$NaCl, cm$^{-1}$) 2371 (s), 1616(w), $^1$H NCR (CDCl$_3$, 300 MHz): δ 7.15 (d,J=8.4 Hz, 1 H), 6.93 (d,J=8.1 Hz, 1 H), 6.57 (br s, 1 H), 6.33 (s, 1 H), 5.79 (AB, J=1.5 Hz, 1 H), 5.74 (AB,J=1.5 Hz, 1 H), 4.81 (d, J=12.0 Hz, 1 H), 4.34 (s, 1 H), 4.07 (dd,J=12.3 Hz, 2.7 Hz, 1 H), 3.85 (s, 3 H), 3.71 (s, 3 H), 3.16 (s, 3 H), 3.05–2.81 (m, 4 H), 2.53 (s, 3 H). HRMS (FAB) Calcd for C$_{22}$H$_{28}$BLiNO$_6$(M+Li)$^+$:420.2170, Found 420.2173.

The synthesis of 1,3-dihydro-4,5-dimethoxy-1-[1-(8-methoxy-2-methyl-6,7-methylenedioxy-1,2,3,4-tetrahydroixoquinolinyl)]isobenzofuran (4):

Compound 3 (450 mg. 1.10 mmol) was refluxed in 15 mL of 20% aqueous KOH solution for 2 h. The reaction mixture was cooled to room temperature, neutralized with 2 N HCl to PH=7 and extracted with CHCl$_3$. The organic phase was washed with brine, dried with MgSO4 and concentrated. Compound 4 was crystallized from Et$_2$O (220 mg, 50%). $^1$H NCR (CDCl$_3$, 300 MHz): delta 6.72 (d,J=8.4 Hz, 1 H), 6.32 (s, 2 H), 5.88 (m, 2 H), 5.63 (br s, 1 H), 5.02 (br s, 2 H), 4.40 (br s, 1 H), 3.82 (s, 3 H), 3.81 (s, 3 H), 3.75 (s, 3 H), 3.14 (br s, 1H), 2.64 (br s, 3 H) 2.60–2.43 (m, 3 H).

EXAMPLE 4

-continued

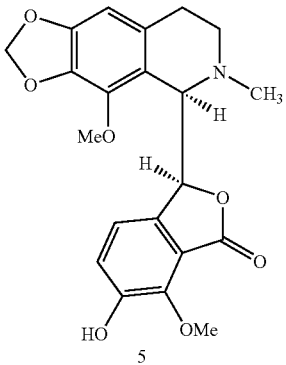

5

The synthesis of compound 5:

(SAR)-Noscapine (826 mg, 2.0 mmol, 1.0 equiv.) was dissolved in 25 mL of CH$_2$Cl$_2$. This solution was added dropwise to a 1.0 M solution of borane trichloride in CH$_2$Cl$_2$ (8.0 mL, 8.0 mmol, 4.0 equiv.) at −78° C. After 5 h, the reaction was quenched with saturated aqueous NaHCO3 (10 mL) and warmed to room temperature. The reaction mixture was extracted with EtOAc (50 mL×3), the combined organic phases were washed with brine (40 mL), dried with MgSO$_4$ and concentrated.

The obtained white solid was dissolved in acetone (50 mL) and H$_2$O (25 mL). This solution was treated with barium carbonate (1.55 g, 7.84 mmol) and refluxed for 3 h. After cooling to room temperature, the reaction mixture was filtered. The filtrate was treated with 1 N HCl until PH=2, then extracted with EtOAc (50 mL×3). The combined extracts were washed with brine, dried over MgSO$_4$ and concentrated. Crystallization (CH$_2$CL$_2$-Et$_2$O) was performed for the resulting off-white solid to give 5 as a silver gray solid (340 mg, 43%). IR(CH$_2$CL$_2$, NaCL, cm$^{-1}$) 3431 (s), 1767 (s). $^1$H NCR(CDCl$_3$, 300 MHz): δ 7.57 (br s, 1 H), 7.27 (br s, 1 H), 6.57 (br s, 1 H), 6.33 (s, 1 H), 5.82 (s, 1 H), 5.78 (s, 1H), 5.11 (br s, 1 H) 4.08 (br s, 1 H), 3.94 (s, 3 H), 3.87 (s, 3 H), 3.33 (m, 1 H), 3.20 (s, 3 H), 3.00 (m, 1 H), 2.82 (m, 2 H). $^{13}$CNMR (CDCl$_3$, 75.5 (MHz): δ 166.3, 152.4, 150.1, 147.3, 139.8, 138.9, 133.4, 126.2, 119.3, 118.8, 116.9, 106.7, 102.3, 100.9, 78.5, 61.9, 58.2, 56.8, 45.2, 39.9, 21.4.

EXAMPLE 5

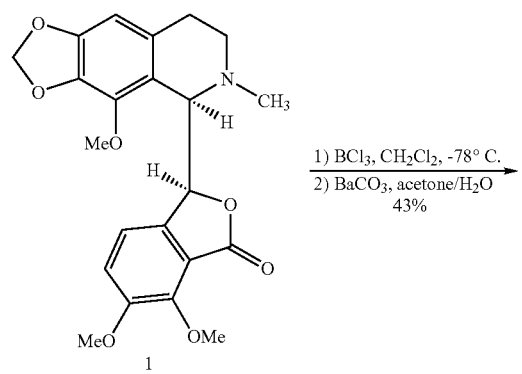

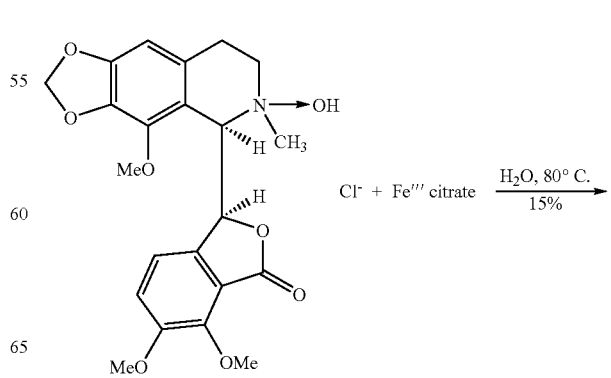

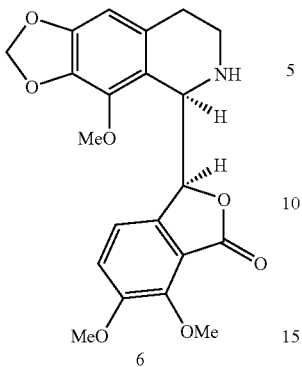

6

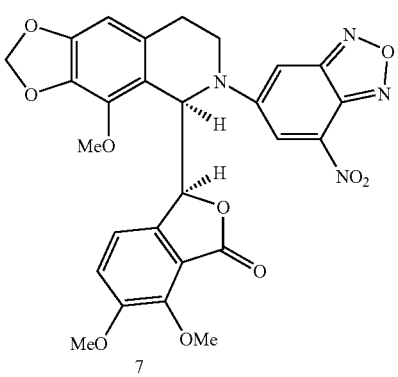

7

Ferric citrate (10.5) was dissolved in 200 mL of H₂O. Citric acid was added to make pH=2. This solution was added to noscapine N-oxide HCl salt (6.0 g) [Uhrin, D. et al., Collect. Czech. Chem. Commun. 54:498(1989)] and the mixture was heated to 85° C. for 3 h. After cooling to room temperature, the solution was treated with saturated Na₂CO₃ solution until pH=9 and extracted with CHCl₃ (200 mL×4). The combined organic phases were washed with brine, dried with anhydrous MgSO₄ and concentrated. The resulting oil was purified by flash chromatography (SiO2, 3×25 cm, 75% EtOAc in hexane) to give 6 as a yellow oil (793 mg, 15%), TLC (silica gel, 75% EtOAc in hexane, $R_f$=0.25); IR(CH₂Cl₂,NaCl, cm⁻¹)3370(w), 1758(s); ¹H NCR (CDCl₃, 300 MHz):): δ 6.92 (d,J=8.1 Hz, 1 H), 6.29 (s, 1 H), 5.93–5.91 (m, 3 H), 5.87 (d,J=3.9 Hz 1 H), 4.80 (d,J=3.9 Hz, 1 H), 4.04 (s, 3 H), 4.02 (s, 3 H), 3.80 (s, 3 H), 3.59–2.55 (m, 1 H), 2.50–2.38 (m, 1H), 2.30–2.38 (m, 1 H), 2.30–2.22 (m, 1 H), 2.15–2.07 (m, 1H), 1.96 (br s, 1 H). ¹³CNMR (CDCl₃, 75.5 MHz):): δ 168.4, 152.1, 148.3, 147.8, 141.0, 140.3, 134.1, 131.9, 119.5, 118.4, 117.5, 116.9, 103.1, 100.7, 80.6, 62.2, 59.4, 56.6, 52.7, 39.5, 29.6, HRMS (FAB) Calcd for $C_{21}H_{21}LiNO_7(M+Li)^+$; 406.1478. Found 406.1477. Anal. Calcd. For $C_{21}H_{21}NO_7$:C, 63.15; H, 5.30; N, 3.51. Found: C, 63.35; H, 5.45; N, 3.42.

EXAMPLE 6

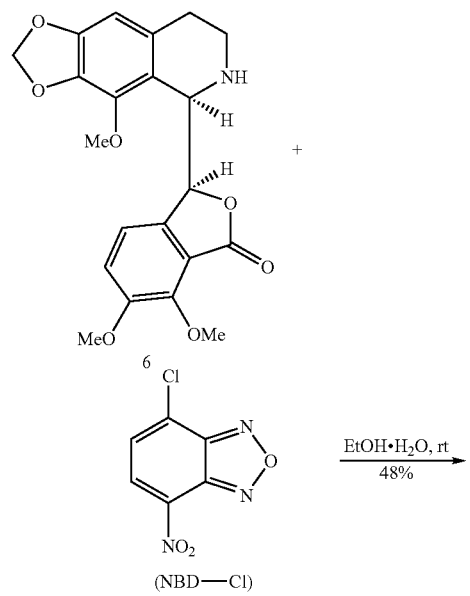

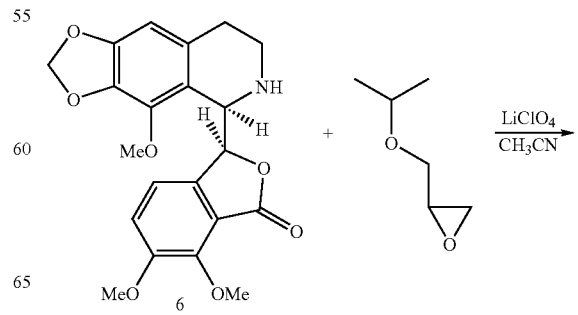

To an ETOH (15 mL) solution of amine 6 (160 mg, 0.40 mmol, 1.0 equiv.) was added 30 mL of Na₂B₄O₇ (1.14 g) buffer and NBD-CL (80 mg, 0.4 mmol, 1.0 equiv.). The reaction mixture was stirred at room temperature for 15 h. Evaporation of ETOH left a dark orange slurry which was extracted with CHCl₃ (70 mL×2). The combined organic phases were washed with brine, dried with MgSO₄ and concentrated. The resulting green oil was purified by flash chromatography (SiO₂, 3×15 cm, 65% EtOAc in hexane) to give an orange solid which was recrystallized from CH₂Cl₂ and hexane to give 7 as an orange crystal (108 mg, 48%). TLC (silica gel, 65% EtOAc in hexane, $R_f$=0.65); mp=1.94–1.95° C. (CH₂Cl₂, NaCl, cm⁻¹) 1765(s), 1616(m), 1540(s), 1500(s), 1287(s), 1261(m). ¹H NCR (CDCl₃, 300 MHZ);): δ 8.53 (d,J=9.0 Hz, 1 H), 7.41 (br d,J=7.8 Hz, 1 H), 7.29 (d,J=8.4 Hz, 1 H), 7.00 (br s, 1 H), 6.48 (d,J=2.7 Hz, 1 H), 6.44 (s, 1 H), 6.04 (d,J=2.7 Hz, 1 H), 5.90 (d,J=7.5 Hz, 2 H), 4.02 (s, 3H), 3.95 (s, 3 H), 3.81 (m, 1 H), 3.76 (s, 3 H), 3.70–3.50 (m, 2 H), 3.02–2.93 (m, 1 H). ¹³C NCR (CDCl₃, 75.5 Hmz):): δ 166.7, 152.8, 149.6, 147.9, 145.1, 145.0, 144.7, 139.5, 138.7, 135.3, 133.7, 130.4, 123.7, 119.0, 118.7, 118.1, 113.4, 102.9, 102.4, 100.9, 81.9, 62.2, 59.1, 58.1, 56.8, 46.5, 27.8. HRMS(FAB) Calcd for $C_{27}H_{22}LiN_4O_{10}(M+Li)^+$:569.1496. Found 569.1472. Anal. Calcd. For $C_{27}H_{22}N_4O_{10}$:C, 57.65; H, 39.1; N, 9.96. Found: C, 57.85; H, 4.04; N, 9.81.

EXAMPLE 7

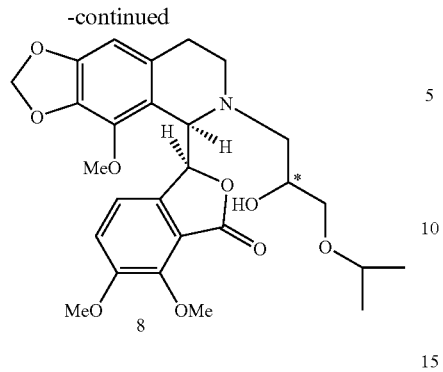

8

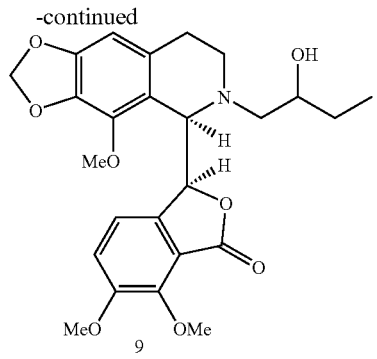

9

A CH$_3$CN (2 mL) solution of glycidyl isopropyl ether (50 µL)\, 0.40 mmol, 1.0 equiv.) was treated with anhydrous LiClO$_4$ salt (43 mg, 0.40 mmol, 1.0 equiv.) and stirred for about 10 min. until a clear solution was observed. This solution was treated with an CH$_3$CN(3 mL) solution of compound 6 (160 mg, 0.40 mmol, 1.0 equiv.) at room temperature. The mixture was refluxed for 24 h, cooled to room temperature, washed with H$_2$O and extracted with Et$_2$O (40 mL×3). The combined organic phases were washed with brine, dried with MgSO$_4$ and concentrated. The resulting orange oil was purified by flash chromatography (SiO$_2$, 2×15 cm, 50% EtOAc in hexane) to give 8 as a yellow oil which is a mixture of the two diastereomers (1:1 ratio, 172 mg, 83%), TLC (silica gel, 50% EtOAc in hexane, R$_f$=0.50); IR (CH$_2$Cl$_2$,NaCl,cm$^{-1}$) 3450(m), 1761(s), 1498 (m), 1478(m). $^1$H NCR (CDCl$_3$, 300 MHz):): δ 6.96 (d,J=8.4 Hz, 2 H), 6 30 (s, 2 H), 6.24 (t,J=8.4 Hz, 2 H), 5.90 (s, 4 H), 5.73 (d,J=4.S Hz, 1 H), 5.67 (d,J=4.2 Hz, 1 H), 4.47 (d,J=4.2 Hz, 1 H), 4.42 (d,J=4.5 Hz, 1 H), 4.06 (s, 3 H), 4.05 (s. 3 H), 3.97 (s, 3H), 3.96 (s, 3 H), 3.82 (s, 6 H), 3.56 (d of sept,J=6.0 Hz, 2 H), 3.41 (m, 4 H),3.0 (br s,2 H),2.74–2.00 (m, 14 H), 1.12(t,J=5.7 Hz, 12 H). $^{13}$C NCR (CDCl$_3$, 75.5 MHz):): δ 167.9, 167.8, 152.2 (2 C), 148.5 (2 C), 148.1 (2 C), 141.2, 141.0, 140.5, 140.4, 133.8, 133.7, 130.9, 130.5, 119.3, 119.0, 118.4 (2 C), 117.5 (2 C), 116.3, 115.8, 102.7, 102.6, 100.7, 100.6, 80.8, 80.1, 71.9, 71.8, 70.4, 70.1, 68.0, 67.8, 62.3, 62.2, 60.5(2C), 59.4, 59.2, 58.6, 58.5, 56.7 (2 C), 46.2, 44.7, 24.8, 24.3, 22.0 (2 C), 21.9 (2 C). Anal. Calcd. for C$_{27}$H$_{33}$NO$_9$:C, 62.90; H, 6.45; N, 2.72. Found: C, 62.97; H, 6.45; N, 2.64.

EXAMPLE 8

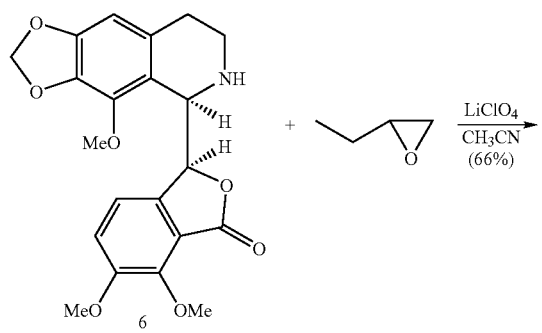

A CH$_3$CN (2 mL) solution of 1,2-epoxybutane (114 µL, 1.32 mmol, 3.3 equiv.) in a sealed tube was treated with anhydrous LiClO$_4$ salt (43 mg, 0.40 mmol, 1.0 equiv.) and stirred for 10 minutes until a clear solution was observed. This solution was treated with a CH$_3$CN (3 mL) solution of compound 6 (160 mg, 0.40 mmol, 1.0 equiv.) at room temperature. The mixture was heated at 115° C. for 10 h., cooled to room temperature, washed with H$_2$O and extracted with Et$_2$O (50 mL×3). The combined organic phases were washed with brine, dried with MgSO$_4$ and concentrated. The resulting yellow oil was purified which is a mixture of the two diastereomers (1:1 ratio, 125 mg, 66%). TLC (silica gel, 65% EtOAc in hexane, R$_f$=0.60); IR(CH$_2$Cl$_2$,NACl,cm$^{-1}$) 3523(s), 1758(s), 1622(m). $^1$H NCR(CDCl$_3$, 300 MHz):): δ 6.99 (d,J=8.1 Hz, 2 H), 6.31 (s, 1 H), 6.30 (s, 1 H), 6.26 (d,J=8.4 Hz, 1 H), 6.25 (d,J=8.4H, 1 H), 5.90 (s, 4 H), 5.79 (d,J=4.5 Hz, 1 H), 5.68 (d,J=3.9 Hz, 1 H), 4.48 (d,J=3.9 Hz, 1 H), 4.40 (d,J=4.5 Hz, 1 H), 4.07 (s, 3 H), 4.06 (s, 3 H), 3.98 (s, 6 H), 3.83 (s, 6 H), 3.66–3.53 (m, 2H), 3.20 (br s, 2 H), 2.68–2.38 (m, 8 H), 2.23–2.10 (m, 4H), 1.42 (m, 4 H), 0.95 (t,J=6.9 Hz, 3 H), 0.93 (t,J=7.2 Hz, 3 H). $^{13}$C NCR (CDCl$_3$ 75.5 MHz):): δ 168.0, 167.7, 152.3, 152.2, 148.6 (2 C), 148.2, 148.1, 141.2, 140.9, 140.6, 140.3, 133.9, 133.7, 130.9, 130.1, 119.3, 118.8, 118.5 (2 C), 117.4 (2 C), 116.4, 115.4, 102.8, 102.5, 100.7, 100.6, 81.1, 79.6, 68.9, 68.7, 62.5, 62.3, 62.2, 61.3, 61.2, 59.3, 59.2, 57.5, 56.7 (2 C), 46.4, 44.0, 27 5, 27.1, 25.1, 23.7, 10.0, 9.8. Anal. Calcd. for C$_{25}$H$_{29}$NO$_8$: C, 63.68; H, 6.20; X, 2.97. Found: C, 63.68; H, 6.18; N, 2.90.

EXAMPLE 9

Noscapine Arrests Hela and Thymocyte Cells at M Phase

Hela cells were grown in DMEM supplemented with 10% fetal calf serum, 1 mM L-glutamine and 1% penicillin/-streptomycin. The tumor cell line E.G7-OVA (H-2$^b$) [Moore, M. W., et al., Cell 54,777 (1988)] was grown in RPMI 1640 with 10% fetal calf serum, 1% sodium pyruvate, 1 mM L-glutamine, 0.1% gentamycin, 50 µM β-mercaptoethanol. Cells were grown at 37° C. in a 5% CO$_2$ atmosphere. Cell viability was assessed by trypan blue exclusion analysis. Cell numbers were determined using a hemacytometer. C57BL/6(H-2$^b$) mice, 8 to 12 weeks of age, were obtained from Harian Sprague Dawley, Inc. (Indiananapolis, Ind.). Mice were maintained on standard laboratory chow and water ad libitum in a temperature and light controlled environment. For immunofluorescence, both Hela and thymocyte cells were treated identically except the Hela cells were grown onto glass coverslips while EL4 thymocytes were put on glass coverslips after fixation. Cells in 10 ml medium were incubated with 2 µl DMSO or 20 µM Noscapine (2 µl 0.1 M DMSO solution) respectively. After 24 hr, cells were fixed with cold (−20° C.) methanol for 5 min., then rehydrated by PBS for 1 min. Nonspecific sites were blocked by incubating with 200 µl of 1% bovine serum albumin (BSA) in phosphate buffered saline (PBS) at 37° C. for 15 minutes. A mouse monoclonal antibody against α-tubulin was diluted 1:200 in PBS containing 1% BSA and incubated (200 µl) with the coverslips at 37° for 1 hr. Then cells were washed with 1% BSA-PBS solution for 10 min. at room temperature before incubating with a 1:200 dilution of a rhodamine labeled goat anti-mouse IgG antibody at room temperature for 45 min., then the coverslips were rinsed by 1% BSA/PBS solution for 10 min. and labeled by DAPI (4',6-diamino-2-phenyliudole) for another 10 min. at room temperature. The coverslips containing the cells were then mounted with a solution containing 0.01% 1,4-diazobicyclo (2,2,2) octane. Cells were examined with a fluorescence microscope. The flow cytometric evaluation of the cell cycle status was performed according to a modification of as described in Empey, D. W., et al., Eur. J. Clin. Pharmacol. 16, 393 (1979). Briefly, untreated or noscapine-treated cells were centrifuged, washed twice with ice-cold PBS, and fixed in 70% ethanol. Tubes containing the cell pellets were stored at −20° C. for at least 24 hr. Following this, the cells were centrifuged at 1000×g for 10 min. and supernatant was discarded. The pellets were resuspended in 30 µl phosphate-citrate buffer at room temperature for 30 min. Cells were then washed with 5 ml PBS and incubated with propidium iodide and RNase (20 mg/ml PI and 20 mg/ml RNase A in PBS) for 30 min. The samples were read on a cytometer.

Results show that by immunofluorescence, with an antibody specific for alphatubulin, that after treatment with noscapine, microtubule arrays are arrested in M phase in Hela and thermocyte cells. Flow cytometric analysis of DNA content showed consistent results.

EXAMPLE 10

Noscapine Initiates Apoptosis

Oligonucleosomal fragmentation of genomic DNA was determined according to Walton, M. I. et. al., Cancer. Res. 53, 1853 (1993). An aliquot of $3.3 \times 10^6$ cells in 10 ml medium was incubated with 20 µM Noscapine (2 µ0.1 M DMSO solution) for different time periods ranging from 0 to 24 hr. At the end of incubation, cells were pelleted and washed twice with ice cold PBS, and lysed in 250 µl 1% (v/v) NP 40 detergent containing 0.5 mg/ml proteinase K in PBS solution on ice for 60 min. Samples were centrifuged, and the supernatants were removed and incubated with 5 µl 10 mg/ml RNase A at 37° C. for 40 min. An aliquot of 1 ml anhydrous ethanol was added, tubes were placed at −20° C. for 20 min., then centrifuged to pellet DNA. After the samples were dry, the same amount of DNA (10 µg) was electrophoresed at 80V for 3 hr. through a 2% agarose gel containing ethidium bromide in TAB buffer. DNA bands were visualized under HV light. A 123 bp DNA ladder was used as molecular size marker.

Morphological changes in the nuclear chromatin of cells undergoing apoptosis were detected by staining with 4',6-diamidino-2-phenylindole (DAPI). In brief, $0.5 \times 10^6$ to $3 \times 10^6$ cells were fixed with 4% glutaraledehyde, 0.2% Triton x-100, in PBS and incubated at room temperature for 10 min., then centrifuged at 1000×g for 10 mm., resuspended in 20 µl 0.1% DAPI ethanol. Following 15 min. incubation at room temperature, a 10 µl aliquot was placed on a glass slide, and 400 cells per slide were scored for the incidence of apoptotic chromatin changes with a fluorescence microscope. A TdT-Mediated dUTP nick end labeling assay is used according to Gorczyca, W. et al., Cancer Res. 53, 1945 (1993) and Gavrieli, Y. et al., J. Cell Bio. 119, 493 (1992). An aliquot of $2 \times 10^6$ cells in 10 ml medium were respectively incubated with 2 µl DMSO and 20 µM noscapine (2 µl 0.1 M DMSO solution) for 24 hr. Cells were pelleted and washed with ice-cold PBS twice, lymphocyte cells were fixed in 4% paraformaldehyde in PBS and air dried. The slides were rinsed with P13S and incubated with blocking solution (0.3% $H_2O_2$ in methanol) for 30 min. at room temperature. The slides were rinsed with PBS again and incubated in permeability solution (0.1% Triton x-100 in 0.1% sodium citrate) on ice for 2 min. Then the slides were washed twice with PBS, then 50 µl nick end labeling assay reaction mixture was added on samples and the slides were incubated in a humidified chamber for 60 min. at 37° C. After the slides were rinsed with PBS, 50 µl converter-POD solution was added on samples and incubated for 30 min. at 37° C. The slides were rinsed with PBS for 3 times, then 60 µl DAB substrate solution was added on the samples, and the slides were incubated at room temperature for 10 min. After the slides were rinsed with PBS for another 3 times, coverslips were mounted and analyzed with a light microscope.

Results show progressive DNA degradation with increasing time of noscapine treatment, as measured by gel electrophoresis of fragmented genomic DNA, or by staining of treated cells.

EXAMPLE 11

Inhibition of Tumor Growth by Noscapine

C57BL/6 mice were injected subcutaneously in the right flank with $2 \times 10^6$ E.G7-OVA cells. Three days later, mice were injected intraperitoneally, every day for three weeks, either with 200 µl saline (n=10), or with 3 mg noscapine dissolved in 200 µl saline (n=10). Third group of mice (n=10) was fed 3 mg noscapine via intragastric (i.g.) intubation using a 1 ml syringe fitted with a 20 gauge stainless steel ball point needle. After three weeks, all mice were sacrificed by cervical dislocation. Tumors were removed and weighed. Tumor weights were individually plotted and comparisons between control and treatment groups were analyzed by the Student's t test. Statistical differences were considered significant if p values were less than 0.01. Results showed that mice treated with noscapine had significantly reduced tumor weight.

EXAMPLE 12

Noscapine Causes Apoptosis in Solid Lymphoid Tumors Induced in Mice

Microscopic examination of Haemotoxline and Eosine stained cells showed many cells in noscapine treated mice with apoptotic morphologies.

EXAMPLE 13

Noscapine Induces Conformational Change Upon Binding Tubulin and Promotes Microtube Assembly Phosphocellulose purified bovine brain tubulin was employed throughout these biophysical experiments. Fluorescence titration for determining binding constants was performed according to Peyrot, V. et al., Biochemistry 31, 11125 (1992). In beef, at room temperature, 2 µM tubulin in 100 mM PIPES, 2 mM EGTA, 1 mM MgCl$_2$ was excited at 278 nm, and the fluorescence emission spectra were recorded with bandwidths 2 mn. The fluorescence emission intensity of noscapine at this excitation wavelength was negligible and at the concentration of noscapine used it gave no appreciable inner filter effect. The concentration of noscapine was raised in increments of 0.5 µM, until the decrease in the fluorescence intensity was saturated. The value of the dissociation constant and the number of sites were obtained from Scatchard plots using the equation, r/[L]$_{free}$=n/K$^d$–r/K$_d$, where r is the ratio of the concentration of bound ligand to the total protein concentration and n is the number of binding sites. Circular dichroism (CD) spectra measurements were performed in a spectroscometer, in cells (0.1 cm path) at 25° C. Microtubule assembly was recorded on a spectrophotometer with thermocontroler, The cuvettes (0.4 cm path) containing 100 mM PIPES, 2 mM EGTA, 1 mM MgCl$_2$ and 1 mM GTP (G-PEM buffer), and 20 µM noscapine/DMSO were kept at room temperature before addition of tubulin and shifting to 37° C. Tubulin and noscapine in G-PEM buffer did not show any detectable absorption at 350 nm. The assembly was monitored by measuring the changes in turbidity at 0 5 min. intervals. Noscapine was dissolved in DMSO at 0.8 mM and stocked at 4° C. The final concentration of DMSO was 2.5%.

Results show that noscapine affords fluorescence quenching of tubulin. Scatchard plot analysis showed an apparent dissociation constant (Kd) of 186±0.34×10$^6$ M and a stoichiometry of 0.95±0.02 noscapine molecule per complex of tubulin subunit. There is also saturation of the noscapine induced quenching in tubulin fluorescence intensity. Noscapine promotes tubulin assembly, as measured by increased absorbance at 350 nm of tubulin when treated with noscapine.

EXAMPLE 14

Initiation of Apoptosis by Noscapine and Derivatives

Morphological changes in the nuclear chromatin of HL-60 cells undergoing apoptosis were detected by staining with 4',6-diamidino-2-phenylindole (DAPI). In brief, 0.5× 10$^6$ to 3×10$^6$ cells were fixed with 4% glutaraledebyde, 0.2% Triton x-100, in PBS and incubated at room temperature for 10 min., then centrifuged at 1000×g for 10 min., resuspended in 20 µl 0.1% DAPI ethanol. Following 15 min, incubation at room temperature, at 10 µl aliquot was placed on a glass slide, and 400 cells per slide were scored for the incidence of apoptotic chromatin changes with a fluorescence microscope.

Results show that noscapine, compound 3 and compound 4 initiate apoptosis.

| Compound* | Apoptic Cell Percentage |
|---|---|
| Noscapine, 20 µM in DMSO | 30.17† |
| 3.20 µM in DMSO | 37.28 |
| 4.20 µM in DMSO | 48.32 |
| Noscapine, 50 µM in DMSO | 27 |
| 3.50 µM in DMSO | 39 |
| 4,50 µM in DMSO | 52 |

*All compounds were incubated with HL-60 cells at the indicated final concentrations for 24 hours.
†Two trials were conducted at 20 µM, the result for each trial is shown.

EXAMPLE 15

Noscapine Acts as an Adjuvant Composition.

The model for the study of tumor-specific immunity and tolerance, included transplanted thymoma that expresses a foreign protein, ovalbumin (OVA) subcutaneously into genetically identical mice. Peptides derived from OVA serve as a defined tumor antigen that is presented to the immune system by the MHC class I proteins. This tumor cell line, called E.G7-OVA, does not express co-stimulatory molecules.

The inventors allowed the transplanted tumor to grow for a period of time to mimic the clinical situation. Drug therapy was used to ablate the tumors before testing for immunological response to the tumor. This system was chosen based upon recent work and data in which the antitussive alkaloid, noscapine (7) was determined to be a new antimitotic drug that induces tumor regression (13).

Noscapine shares structural similarities with colchicine and taxol. Like these agents, noscapine binds to microtubules altering their conformation which promotes polymerization that in turn causes arrest of growth in mitosis (13). Noscapine, given parenterally or by gastric gavage, arrested tumor cell growth and induced apoptosis of E.G7-OVA in vivo. Noscapine also caused regression of human breast and bladder tumors in nude mice suggesting that noscapine may also be effective in humans.

To test whether E.G7-OVA tumor induced tolerance, tumors were ablated by treating the mice with noscapine in the drinking water beginning three days after tumor transplantation. Tumors grew in all mice that had received E.G7-OVA without noscapine. The majority of tumors in the mice that received noscapine disappeared and did not return during four months of continuous treatment with the drug (FIG. 1). At four months treatment with noscapine, the surviving mice were healthy and had normal weights and appearance.

Untreated, control B6 mice and noscapine treated mice whose tumors regressed, were injected with OVA in CFA to test whether the tumor had induced tolerance to OVA. OVA-specific antibody responses (FIG. 2A) and cytokine production by CD4+ T cells (FIG. 2B) were identical in these mice suggesting that the tumor did not induce tolerance. Moreover, the OVA-specific CTL response of mice that recovered from the tumor was enhanced by 10- to 30-fold compared to the response of non-tumor bearing controls (FIG. 2C) (14).

From the above results it appears that apoptosis of the tumor induced by noscapine resulted in priming of OVA-specific CTL precursors without significant priming effect on CD4+ T cells or B cells. This is not surprising since E.G7-OVA does not induce antibodies or prime CD4+ T cells as it lacks MHC class II antigens.

Priming of CTL responses by cells that lack co-stimulatory molecules, such as E.G7-OVA, can be achieved by uptake and processing of these cells by macrophages (15, 16). Macrophages then display peptide fragments of the antigen in association with endogenous MHC class I molecules. Such macrophages also display the requisite co-stimulatory molecules. This process is referred to as "cross-priming" (17).

Cross-priming, in general, is relatively inefficient as shown by the fact that the tumors do not normally induce rejection. The inventors believe that Noscapine may enhance antigen uptake by macrophage or enhance expression of co-stimulatory molecules by phagocytic cells such as macrophage and dendritic cells.

Anti-mitotic drugs inhibit division of normal cells as well as tumor cells. However, parenteral administration of noscapine induced no significant histological evidence of toxicity to the kidney, liver, or heart at tumor suppressive doses (FIG. 3), Ke et al. in preparation (14). A few small areas of inflammation were observed in the liver at the 3.0 mg dose of noscapine. The gut and the immune system (bone marrow, thymus, lymph nodes, and spleen), depend upon dividing cells and thus they are very sensitive to the anti-mitotic activity of drugs such as taxol and vincaloids.

Histology of the spleens and lymph nodes from noscapine treated mice showed no alterations from control mice that were fed water acidified to the same pH as the noscapine solution (FIG. 4). The small intestines developed mild edema of the villi and goblet cell hyperplasia in mice treated with noscapine in the drinking water. The number of mitotic figures observed in the crypts of the small intestine were approximately equal in the noscapine treated and in control mice suggesting that arrest in G1 phase did not occur in the normal epithelial cells. In addition, the noscapine treated mice were healthy and of the same weight as the control mice.

Figure 5A:
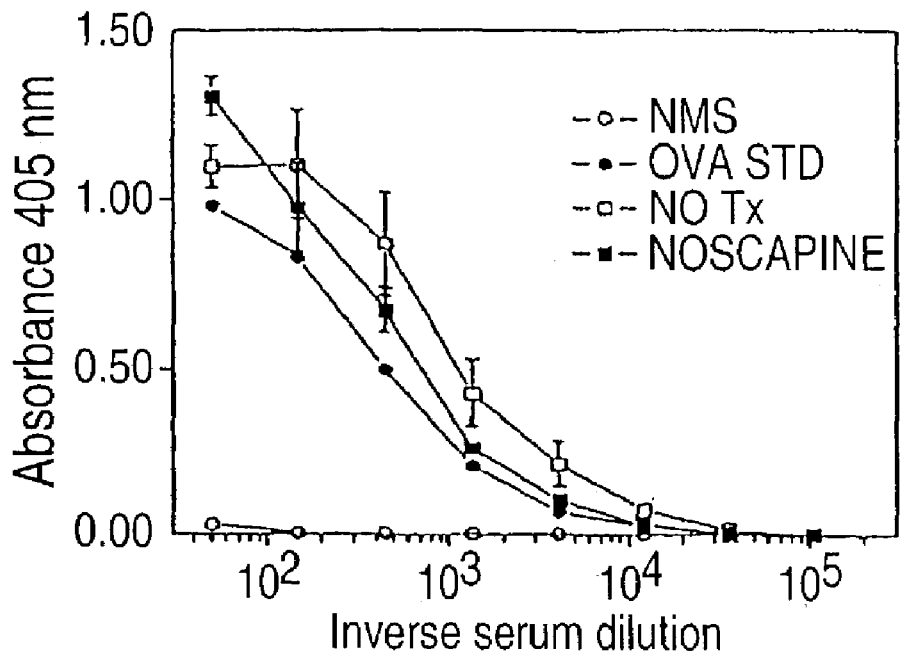
FIG. 5 shows B6 mice were treated with 1.5 mg noscapine/ml in the drinking water or acidified water beginning on day −7 and continuing throughout the experiment. On day 0 all mice were injected with 200 μg OVA in CFA in the foot pad. Mice were bled individually on day 18 and their sera tested for antibody to OVA by ELISA (FIG. 5A). The mice were sacrificed on day 21 and their spleen cells cultured with E.G7-OVA for 6 days and their cytolytic activity measured with $^{51}$Cr labeled cells (FIG. 5B). These results demonstrate that Noscapine exerts no detectable adverse effect on the immune response to OVA in CFA.
Figure 5B:
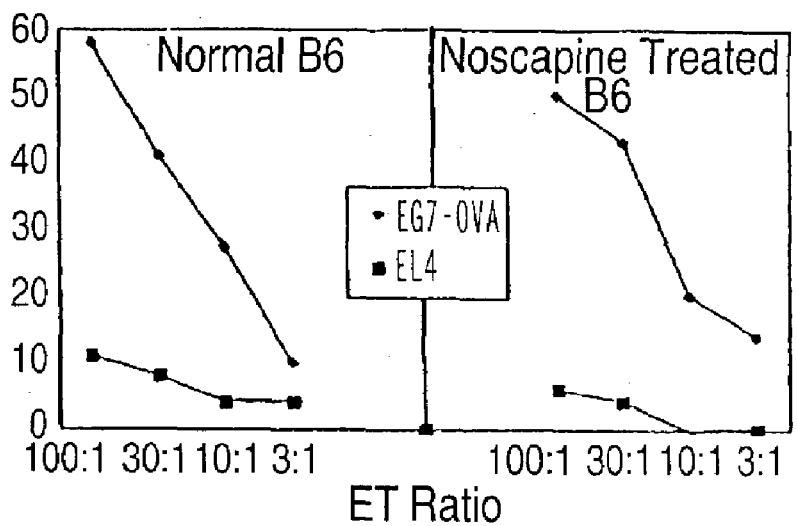

In functional studies, oral noscapine did not inhibit primary antibody (FIG. 5A) or CTL responses (FIG. 5B), which are critically dependent upon proliferation of lymphoid cells (14). The inventors believe that the damage caused to the mitotic apparatus of dividing cells must be repaired by normal cells but not the tumor cells at the tumor suppressive doses. Alternatively, the tumor suppressive effects of Noscapine may be unrelated to the anti-mitotic effect of the drug.

EXAMPLE 16

Noscapine is believed to be useful in treating metastatic tumor growth. To provide the highest systemic doses, the inventors suggest that Noscapine could be delivered by the gastric or the parenteral route. However, for tumors that are known to metastasize preferentially to certain organs, it may be desirable to deliver Noscapine to that local. The inventors believe that Noscapine may inhibit the growth of metastatic tumors as it did for the primary tumor in the above example.

EXAMPLE 17

The inventors believe that Noscapine can augment weak vaccines in a manner similar to the augmented immune response induced to the tumor, E.G7-OVA. On the basis of the tumor experiments, the inventors believe that Noscapine can delivered systematically using either the gastric or parenteral routes whereas the vaccine is usually delivered subcutaneously. However, alternative routes for vaccination should also be augmented by systematic Noscapine. The inventors believe that Noscapine augments cell mediated immune responses to vaccines. Augmented antibody responses may also be obtained.

Any new adjuvant composition drug adds to the limited armamentarium of agents that can be used to treat tumors. Noscapine has promise as a new adjuvant composition, particularly because of the lack of toxicity at therapeutic doses. Recent results suggest that noscapine induced damage to the mitotic apparatus may be reversed or blocked in non-transformed cells.

Furthermore, the ability of noscapine to induce enhanced cytolytic responses to the tumor is completely different from the other anti-mitotic drugs that inhibit the immune responses while inhibiting tumor growth. Thus, noscapine appears to act as an adjuvant to the cellular immune system and the resulting tumor specific immunity. This activity may prevent metastasis of the original tumor or reemergence of a dormant tumor.

From the above, noscapine and the derivatives thereof cited herein can serve as an adjuvant to augment cell mediated immunity to bacteria or viruses that infect host cells that lack co-stimulatory molecules, such as fibro-blasts, cardiac tissues and the pancreas. Thus, noscapine can be administered at the time of infection with live, attenuated vaccines, such as: influenza, malaria, or HIV.

In addition, noscapine can be administered with DNA vaccines to enhance cell mediated and antibody responses. Noscapine can be used for immunization with proteins or polysaccharides because these molecules are poor immunogens by themselves and there aren't many adjuvants approved for use in humans.

The fact that noscapine caused certain human tumors to regress in nude mice suggests that human tumors will be susceptible to the drug. Several types of tumors have been tested.

REFERENCES

1. Davidoff, A. M., J. D. Iglehart, and J. R. Marks. 1992. Immune response to p53 is dependent upon p53/HSP70 complexes in breast cancers. Proc. Natl. Acad. Sci. USA 89:3439.

2. Klein, G. and T. Boon. 1993. Tumor immunology: Present perspectives. Curr. Opin. Immunol. 5:687.

3. Suto, R. and P. K. Srivastava. 1995. A Mechanism for the specific immunogenicity of heat shock protein—chaperoned peptides. Science 269:1585.

4. Blachere, N. E., Z Li, R. Y Chandawarkar, R. Suto, N. S. Jaikaria, S. Basu, Udono, and P. K. Srivastava. 1997. Heat shock protein-peptide complexes, reconstituted in vitro, elicit peptide-specific cytotoxic T lymphocyte response and tumor immunity. J.Exp.Med. 186:1315.

5. Henderson, R. A. and O. J. Finn. 1996. Human tumor antigens are ready to fly. [Review][169 refs]. Adv.Immunol. 62:217.

6. Chambers, C. A. and J. P. Allison. 1997. Co-stimulation in T cell responses. Current Opinion Immunol. 9:396.

7. Pardoll, D. M., P. Golumbek, H. Levitsky, and L. Jaffee. 1992. Molecular engineering of the antitumor immune response. Bone Marrow Transplant. 9 (Suppl 1):182.

8. Baskar, S. 1996. Gene-modified tumor cells as cellular vaccine. Cancer Immunology, Immunotherapy 43:165.

9. Liu, B., E. R. Podack, J. P. Allison, and T. R. Malek. 1996. Generation of primary tumor-specific CTL in vitro to immunogenic and poorly immunogenic mouse tumors. J. Immunol. 156: 1117.

10. Sotomayor, E. M., I. Borrello, and H. I. Levitsky. 1996. Tolerance and cancer: a critical issue in tumor immunology. Critical Reviews in Oncogenesis 7:433.

11. Staveley-O'Carroll, K., E. Sotomayor, J. Montgomery, I. Borrello, L. Hwang, S. Fein, D. Pardoll, and H. Levitsky. 1998. Induction of antigen-specific T cell energy: An early event in the course of tumor progression. Proc. Natl. Acad. Sci. USA 95:1178.

12. Bogen, B. 1996. Peripheral T cell tolerance as a tumor escape mechanism: deletion of CD4+ T cells specific for a monoclonal immunoglobulin idiotype secreted by a plasmacytoma. Eur J. Immunol. 26:2671.

13. Ye, K., Y. Ke, N. Keshava, J. Shanks, J. A. Kapp, R. R. Tekmal, J. Petros, Joshi, and HC. 1998. Opium alkaloid noscapine is an antitumor agent that arrests metaphase and induces apoptosis in dividing cells. Proc. Natl. Acad. Sci. USA 95:1601.

14. Ke, Y., K. Ye, H E. Grossniklaus, D. R. Archer, H. Joshi, and J. A. Kapp. 1998. Oral administration of noscapine arrests the growth of a subcutaneous thymoma without significant toxicity to normal cells or immunosuppresion. (In preparation).

15. Debrick, J. E., P. A. Campbell, and U. D. Staerz. 1991. Macrophages as accessory cells for class I MHC-restricted immune responses. J. Immunol. 147:2846.

16. Ke, Y., Y. Li, and J. A. Kapp. 1995. Ovalbumin injected with complete Freund's adjuvant stimulates cytolytic responses. Eur. J. Immunol. 25:549.

17. Carbone, F. R. and M. J. Bevan. 1990. Class I-restricted processing and presentation of exogenous cell-associated antigen in vivo. J ExpMed 171:377.

The purpose of the above description and examples is to illustrate some embodiments of the present invention without implying any limitation. It will be apparent to those of skill in the art that various modifications and variations may be made to the composition and method of the present invention without departing from the spirit or scope of the invention. All patents and publications cited herein are incorporated by reference in their entireties.

We claim:

1. A method of enhancing a mammal's protective immune response to a vaccine antigen, comprising the steps of administering to said mammal an immunogenic amount of the vaccine antigen and a immunogenicity-augmenting amount of noscapine in concurrent or sequential combination with said vaccine antigen, wherein the vaccine antigen is selected from the group consisting of small pox, yellow fever, distemper, chlorea, fowl pox, antivenom, scarlet fever, diptheria toxoid, tetanus toxoid, whooping cough, influenza, rabies, mumps, measles and poliomyelitis.

2. A method of augmenting cell mediated protective immunity in a host to bacteria, or viruses that infect host cells that lack co-stimulatory molecules, the method comprising administering to the host (1) a noscapine compound of the following formula:

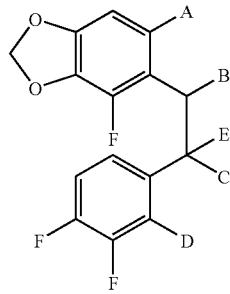

wherein:

A is (i)

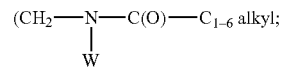

and W is $C_{1-6}$ alkyl; or (ii)

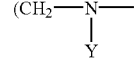

and forms a six membered ring with B, said ring containing one nitrogen;

Y is (a) $C_{1-6}$ alkyl, or H;

(b) $C(O)—C_{1-6}$ alkyl;

(c)

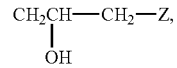

wherein Z is $C_{1-6}$ alkyl or $O—C_{1-6}$ alkyl;

(d) aryl; or (e) a heterocycle selected from the group consisting of piperidinyl, piperazinyl, 2-oxopiperazinyl, 2-oxopiperidinyl, 2-oxopyrrolodinyl, 2-oxoazepinyl, azepinyl, pyrrolyl, 4-piperidonyl, pyrrolidinyl, pyrazolyl, pyrazolidinyl, imidazolyl, imidazolinyl, imidazolidinyl, pyridyl, pyrazinyl, pyrimidinyl, pyridazinyl, oxazolyl, oxazolidinyl, isoxazolyl, isoxazolidinyl, morpholinyl, thiazolyl, thiazolidinyl, isothiazolyl, quinuclidinyl, isothiazolidinyl, indolyl, quinolinyl, isoquinolinyl, benzimidazolyl, thiadiazoyl, benzopyranyl, benzothiazolyl, benzoxazolyl, furyl, tetrahydrofuryl, tetrahydropyranyl, thienyl, benzothienyl, thiamorpholinyl, thiamorpholinyl sulfoxide, thiamorpholinyl sulfone, and oxadiazolyl;

B is a single bond, OH or halo;

C is —OH, or —CH$_2$—and

D is: —OH, —CH$_2$-halo, —CH(O)—, —COOH, —C(O)—O—C$_{1-6}$ alkyl, —(CH$_2$)$_n$—, —CHOH—, wherein n is an integer and is 1, 2, or 3;

or wherein C and D form a 5-membered lactone or lactam ring;

E is —H or —CH$_3$; and

F is —OH or —OCH$_3$, or pharmaceutically acceptable salts thereof, and (2) an attenuated or live vaccine, wherein compound (1) is administered in an effective amount to augment cell mediated immunity in a host to the vaccine (2).

* * * * *